United States Patent
Zhu et al.

(10) Patent No.: US 9,243,364 B2
(45) Date of Patent: Jan. 26, 2016

(54) METHODS OF PRETREATING LIGNOCELLULOSIC BIOMASS WITH REDUCED FORMATION OF FERMENTATION INHIBITORS

(71) Applicant: The United States of America as Represented by the Secretary of Agriculture, Washington, DC (US)

(72) Inventors: JunYong Zhu, Madison, WI (US); Roland Gleisner, Jefferson, WI (US)

(73) Assignee: The United States of America as Represented by the Secretary of Agriculture, Washington, DC (US)

( * ) Notice: Subject to any disclaimer, the term of this patent is extended or adjusted under 35 U.S.C. 154(b) by 0 days.

(21) Appl. No.: 14/299,926

(22) Filed: Jun. 9, 2014

(65) Prior Publication Data

US 2015/0354141 A1 Dec. 10, 2015

(51) Int. Cl.
C12P 7/06 (2006.01)
D21H 17/66 (2006.01)
C12P 7/10 (2006.01)
D21H 11/06 (2006.01)

(52) U.S. Cl.
CPC ........ *D21H 17/66* (2013.01); *C12P 7/10* (2013.01); *D21H 11/06* (2013.01); *C12P 2201/00* (2013.01)

(58) Field of Classification Search
CPC ........................................................ C12P 7/10
See application file for complete search history.

(56) References Cited

U.S. PATENT DOCUMENTS 8,030,039 B1 * 10/2011 Retsina et al. ................ 435/161

OTHER PUBLICATIONS

Kim et al. Bioresource Technology, 2005, 96:1249-1255.*
Nguyen et al. Applied Biochemistry and Biotechnology, 2000, 84-86:561-576.*
Luo X., et al, "Evaluation of Mountain Beetle-Infested Lodgepole Pine for Cellulosic Ethanol Production by Sulfite Pretreatment to Overcome Recalcitrance of Lignocellulose", Industrial Engineering Chemistry Research, vol. 49, 2010, pp. 8258-8266.
Zhou H., et al, "Bioconversion of Beetle-Killed Lodgepole Pine Using SPORL: Process Scale-up Design, Lignin Coproduct, and High Solids Fermentation without Detoxification", Industrial Engineering Chemistry Research, vol. 52, 2013, pp. 16057-16065.
Zhang C., et al, "Using low temperature to balance enzymatic saccharification andfuran formation during SPORL pretreatment of Douglas-fir", Process Biochemistry, vol. 49, 2014, pp. 466-473.
Zhu J.Y., et al, "Conceptual net energy output for biofuel production from lignocellulosic biomass through biorefining" Progress in Energy and Combustion Science, vol. 38, 2012, pp. 583-598.
Stephen, J.D., et al, "Biomass logistics as a determinant of second generation biofuel facility scale, location and technology selection", Biofuels, Bioproductions, and Biorefining, vol. 4 2010, pp. 503-518.
Kirschbaum, M.U.F., "To sink or burn? A discussion of the potential contributions of forests to greenhouse gas balances through storing carbon or providing biofuels", Biomass and Bioenergy, vol. 24, 2003, pp. 297-310.
Gan, J., Smith, C. T., "Availability of logging residues and potential for electricity production and carbon displacement in the USA", Biomass and Bioenergy, vol. 30, 2006, pp. 1011-10.
Wang, Z., et al, "Lignosulforiate-mediated cellulase adsorption: enhanced enzymatic saccharification of lignocellulose through weakening nonproductive binding to lignin", vol. 6, 2013, pp. 1-10.
Lou, H., et al, "pH-Induced Lignin Surface Modification to Reduce Nonspecific Cellulase Binding and Enhance Enzymatic Saccharification of Lignocelluloses", ChemSusChem, vol. 6, 2013, pp. 919-927.
Lan T.Q., et al, "Enzymatic Saccharification of Lignocelluloses Should be Conducted at Elevated pH 5.2-6.2", Bioenerg. Res., vol. 6. 2013, pp. 476-485.
Lin, S.Y., Dence C.W, "Methods in Lignin Chemistry", Springer-Verlag, 1992, pp. 33-61.
Wood, TM, Bhat, KM, "Method in Enzymology", Academic Press Inc., vol. 160, 1988, pp. 87-112.
Perlack, RD, Stokes, BJ, "Billion-Ton Update: Biomass Supply for a Bioenergy and Bioproducts Industry," Oakridge National Laboratory, DOE, 2011.

* cited by examiner

*Primary Examiner* — Bin Shen
(74) *Attorney, Agent, or Firm* — John D. Fado; Lesley D. Shaw; Janet I. Stockhausen

(57) ABSTRACT

Methods of pretreating lignocellulosic biomass in preparation for enzymatic saccharification and fermentation are provided. Also provided are methods of producing ethanol from lignocellulosic biomass via enzymatic saccharification and fermentation that utilize the pretreatment method. In the methods, pretreatment is conducted in two stages. In the first stage, the lignocellulosic biomass is treated in a mildly acidic or near pH-neutral solution to promote delignification and lignin sulfonation, while minimizing the formation of degradation products that inhibit subsequent enzymatic saccharification and/or fermentation. In the second stage, the pH of the solution is decreased in order to promote the depolymerization and dissolution of hemicelluloses in the lignocellulosic biomass.

26 Claims, 21 Drawing Sheets

Table III.A. Key Components of Starting Lignocellulosic Biomass from Douglas Fir Forest Residue (1000 Kg)

| Component | K Lignin | Arabinan | Galactan | Glucan | Xylan | Mannan | Glucan+Mannn | Xylan | Total |
|---|---|---|---|---|---|---|---|---|---|
| Content (kg) | 293.0 | 10.4 | 20.0 | 409.7 | 57.0 | 96.7 | 563.4 | | 886.8 |

Table III.B. Key Components in Pretreated Biomass Solids and Process Liquor

| Component | Biomass Solids | | | | | Process Liquor | | | | | | | |
|---|---|---|---|---|---|---|---|---|---|---|---|---|---|
| | Glucan | Xylan | Mannan | K Lignin | Solids yields a | Glucose as glucan | Xylose as xylan | Mannose as mannan | K Lignin b | Furfural as pentosan | HMF as hexosan | Yield c | Total Yield |
| Initial Pretreatment pH = 4.0 | | | | | | | | | | | | | |
| t0A4B12 | 388.4 | 13.7 | 15.8 | 170.6 | 612.7 | 21.8 | 17.7 | 54.6 | 120.3 | 5.0 | 9.3 | 228.7 | 841.4 |
| t25A4B12 | 405.6 | 22.7 | 23.7 | 130.1 | 603.9 | 10.0 | 13.5 | 32.8 | 160.8 | 2.2 | 4.0 | 222.9 | 826.8 |
| t35A4B12 | 410.7 | 20.4 | 21.8 | 137.7 | 616.5 | 15.7 | 15.1 | 38.2 | 153.2 | 2.0 | 3.8 | 228.0 | 844.5 |
| t45A4B12 | 387.8 | 21.0 | 25.7 | 131.9 | 622.3 | 9.1 | 14.2 | 30.9 | 159.0 | 2.0 | 2.9 | 218.1 | 840.4 |
| Initial Pretreatment pH = 10.0 | | | | | | | | | | | | | |
| t0A14S15 | 321.0 | 13.3 | 14.5 | 194.7 | 586.4 | 13.6 | 6.0 | 28.2 | 96.2 | 9.3 | 22.2 | 175.5 | 761.9 |
| t25A14S15 | 298.0 | 25.3 | 62.6 | 153.4 | 602.5 | 0.6 | 0.4 | 1.1 | 137.5 | 1.8 | 1.5 | 142.9 | 745.4 |
| t45A14S15 | 318.1 | 29.2 | 70.9 | 155.5 | 640.0 | 2.5 | 8.1 | 7.7 | 135.4 | 3.8 | 3.2 | 160.7 | 800.7 |

FIG. 19

Table V.A. Key Components of Starting Lignocellulosic Biomass (1000 Kg)

| Component | K Lignin | Glucan | Xylan | Mannan |
|---|---|---|---|---|
| Content (kg) | 293 | 410 | 57 | 97 |

Table V.B. Key Components in Pretreated Biomass Solids and Process Liquor

| | Biomass Solids (From Blow Tank + Leftover) | | | | | Process Liquor As Collected/(Solids) | | | | | |
|---|---|---|---|---|---|---|---|---|---|---|---|
| Component | Glucan | Xylan | Mannan | K Lignin | Solids Yield | Glucan | Xylan | Mannan | K Lignin | Furfural as pentosan | HMF as hexosan | Yield |
| Content (kg) | 439 | 39 | 72 | 208 | 1012 | 1.9/(2.4) | 2.3/(0.8) | 2.4/(3.9) | .../(0.4) | 0.2 | 0.2 | 271/(51) |

FIG. 20

METHODS OF PRETREATING LIGNOCELLULOSIC BIOMASS WITH REDUCED FORMATION OF FERMENTATION INHIBITORS

BACKGROUND

Lignocellulosic biomass, as a structural material, has natural resistance to enzymatic deconstruction for production of fermentable sugars. Pretreatment, a step to remove this recalcitrance, increases the cellulose accessibility to cellulase for efficient saccharification of the polysaccharides in lignocelluloses. However, most promising and commonly practiced acidic pretreatments, such as dilute acid, Sulfite Pretreatment to Overcome Recalcitrance of Lignocellulose (SPORL), Organosolv and $SO_2$-catalyzed steam explosion, can also degrade sugars to undesirable compounds such as furans. Furthermore, these pretreatments can also convert acetyl groups on the hemicellulose backbone into acetic acid. The undesirable sugar degradation products and acetic acid are inhibitive to many microbes and catalysts, such as *Saccharomyces cerevisiae*, during conversion of sugars to biofuel and bioproducts through fermentation and catalytic processes. Removal of the inhibitive compounds through detoxification steps is possible, but at additional cost, which negatively affects production economics.

SUMMARY

Methods of pretreating lignocellulosic biomass are provided. Also provided are methods of producing ethanol from lignocellulosic biomass that include the lignocellulosic biomass pretreatment.

One embodiment of a method of pretreating lignocellulosic biomass comprises the steps of: mixing the lignocellulosic biomass with a sulfite solution having an initial pH of at least about 3 or a hydroxide solution having an initial pH of at least about 3, as measured at room temperature, and maintaining the mixture at a temperature in the range from about 150° C. to about 200° C. for a first treatment period; and subsequently decreasing the pH of the mixture to a pH in the range from about 1 to less than 3 by introducing a pH-reducing agent into the mixture and maintaining the mixture at a temperature in the range from about 150° C. to about 200° C. for a second treatment period to provide a treated product comprising pretreated biomass solids and a process liquor.

One embodiment of a method of producing ethanol from lignocellulosic biomass comprises the steps of: mixing the lignocellulosic biomass with either a sulfite solution having an initial pH of at least about 3 or a hydroxide solution having an initial pH of at least about 3, as measured at room temperature, and maintaining the mixture at a temperature in the range from about 150° C. to about 200° C. for a first treatment period; subsequently decreasing the pH of the mixture to a pH in the range from about 1 to less than 3 by introducing a pH-reducing agent into the mixture and maintaining the mixture at a temperature in the range from about 150° C. to about 200° C. for a second treatment period to provide a treated product comprising pretreated biomass solids and a process liquor; and subjecting the pretreated product to enzymatic saccharification and fermentation to produce ethanol.

Other principal features and advantages of the invention will become apparent to those skilled in the art upon review of the following drawings, the detailed description, and the appended claims.

BRIEF DESCRIPTION OF THE DRAWINGS

Illustrative embodiments of the invention will hereafter be described with reference to the accompanying drawings, wherein like numerals denote like elements.

FIG. 19. Tables of comparisons of yields of key wood components in the recovered solids and liquid hydrolysate after pretreatment at 165° C. for 75 min among respective control and pH profiling runs at two initial pH values of 4.0 and 7.0 from Examples 1 and 2.

FIG. 20. Tables of comparisons of yields of key wood components in the recovered solids and liquid hydrolysate after pretreatment from Example 3.

DETAILED DESCRIPTION

Figure 1:
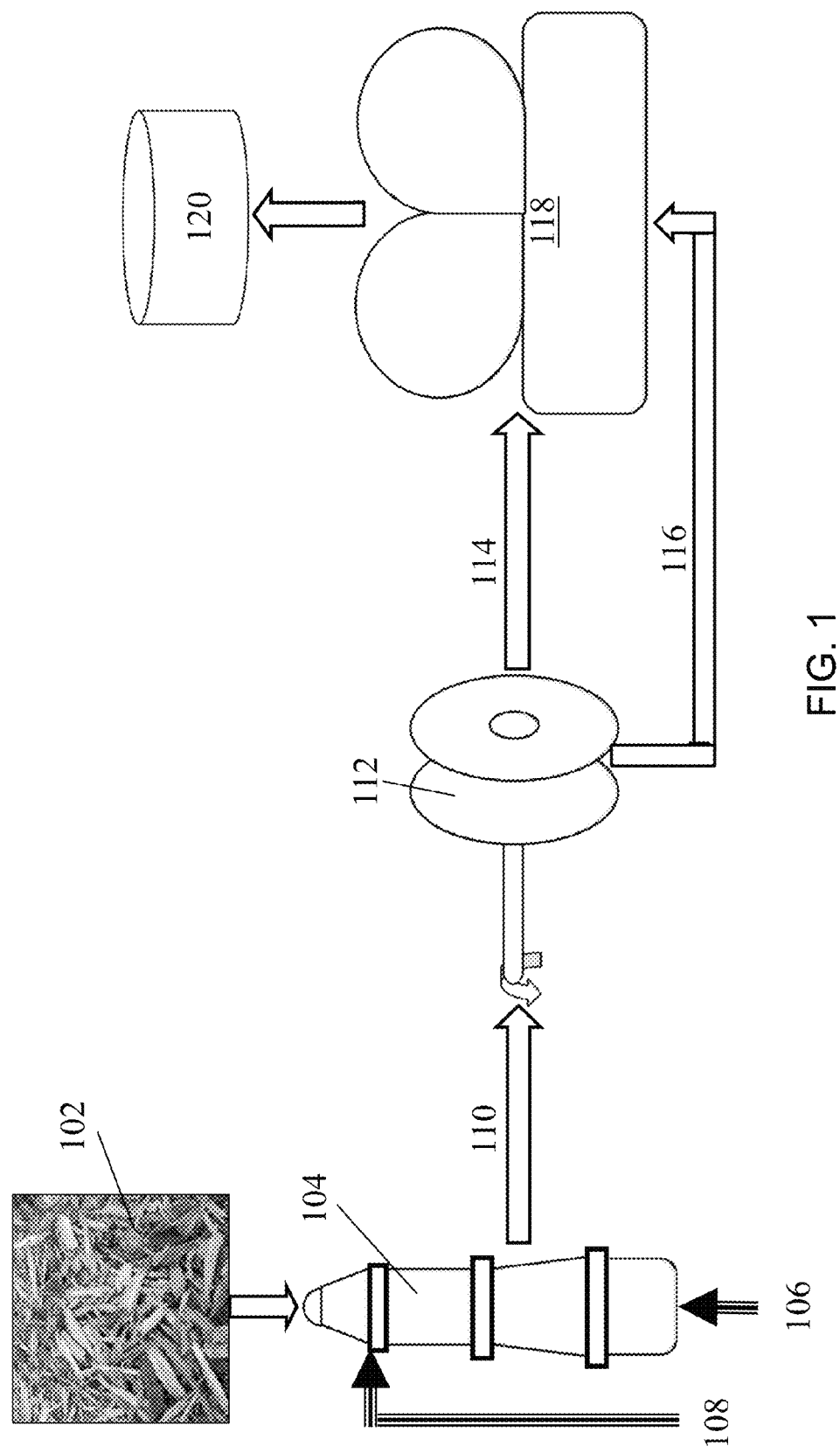
FIG. 1. A schematic flow diagram of one embodiment of a method of converting lignocellulosic biomass into bioethanol.

Methods of pretreating lignocellulosic biomass in preparation for enzymatic saccharification and fermentation are provided. Also provided are methods of producing ethanol from lignocellulosic biomass via enzymatic saccharification and fermentation that utilize the pretreatment method.

In the methods, pretreatment is conducted in two stages with a pH adjustment demarcating the stages. As such, the pretreatments are referred to herein as employing pH profiling. In the first stage, the lignocellulosic biomass is treated in a mildly acidic or near pH-neutral or alkaline solution in order to promote delignification and/or lignin sulfonation, while minimizing the formation of degradation products that inhibit subsequent enzymatic saccharification and/or fermentation. In the second stage, the pH of the solution is decreased in order to promote the depolymerization and dissolution of hemicelluloses in the lignocellulosic biomass. This second stage has a relatively short duration in order to limit production of degradation products. The product of the pretreatment is a highly digestable lignocellulosic substrate for robust enzymatic saccharification. As such, the methods have applications in the field of bioconversion of lignocellulosic biomass for producing sugar, biofuel, and bioproducts.

One embodiment of a method for pretreating lignocellulosic biomass comprises the steps of mixing the lignocellulosic biomass with a sulfite solution or a hydroxide solution having an initial pH of at least 3, as measured at room temperature, and maintaining the mixture at a temperature in the range from about 150° C. to about 200° C. for a first treatment period; and then decreasing the pH of the mixture to a pH in the range from about 1 to less than 3 (for example from 1.2 to 2) by introducing a pH-reducing agent into the mixture and maintaining the mixture for a second treatment period to provide a pretreated product comprising pretreated biomass solids and a process liquor. Bisulfite or sulfite may be used to form the sulfite solution. For solutions using bisulfite, the initial pH may be in the range from about 3 to about 5 (for example, from about 3 to about 4), while for solutions using sulfite, the initial pH may be in the range from about 8 to about 12 (for example from about 9 to about 11).

By using sulfite, which can sulfonate and solubilize lignin at acidic or low pH conditions while simultaneously depolymerizing hemicelluloses, the pretreatment methods can achieve effective delignification and dissolution of hemicelluloses in a narrow pH range of near neutral to mildly acidic, significantly facilitating the practice of the methods without using a large pH range, thereby reducing alkali or acid application for active pH control through acidification or neutralization. However, when the pH-reducing agent is sulfur dioxide, a hydroxide solution may be used because the sulfur dioxide reacts with the hydroxide to form sulfite in solution. When a hydroxide solution is used, the pH of the initial solution may be in the range from about 8 to about 12, or even higher (for example from about 9 to about 12, or even higher).

The lignocellulosic biomass that is used as the starting material is plant matter comprising cellulose and hemicellulose polymers in a crosslinking lignin matrix. The lignocellulosic biomass may be obtained from a variety of sources. For example, the lignocellulosic biomass may be woody biomass from the forestry industry or agricultural biomass. The methods can be used to pretreat lignocellulosic biomass having a very high lignin content, such as biomass from softwoods. In some cases, such lignocellulosic biomass may have a lignin content of at least about 25 percent, based on weight (wt. %). This includes lignocellulosic biomass having a lignin content of at least about 30 wt. %. Prior to undergoing pretreatment, the lignocellulosic biomass starting material may undergo pre-processing to reduce its size and/or water content.

In the initial stage of the pretreatment method, the lignocellulosic biomass starting material is mixed with a solution comprising sulfite ions ("sulfite solution") in a reaction chamber. The sulfite solution can be produced, for example, by bubbling sulfur dioxide through a hydroxide solution to achieve a mildly acidic, near neutral or alkaline initial solution pH in the range from about 3 to about 12, as measured at room temperature. During the first stage of the pretreatment, the mixture is maintained at a temperature in the range from about 150° C. to about 200° C. In some embodiments, the mixture is maintained at a temperature in the range from about 150° C. to about 190° C. during this stage. This includes embodiments in which the mixture is maintained at a temperature in the range from about 160° C. to about 175° C. The lignocellulosic biomass is allowed to react with the sulfite solution for a period of time (the first pretreatment period), whereby it undergoes mainly delignification and/or lignin sulfonation. The optimal duration of the first pretreatment period will vary depending, at least in part, on the reaction temperature—with higher reaction temperatures facilitating shorter pretreatment periods. By way of illustration, the first pretreatment period can have a duration of 90 minutes or less. This includes durations of 75 minutes or less, 60 minutes or less, 45 minutes or less and 25 minutes or less. However, longer durations can also be employed. Guidance for determining a suitable duration for the first pretreatment period can be found in Zhang, Houtman, and Zhu, Using Low Temperature to Balance Enzymatic Saccharification and Furan Formation during SPORL Pretreatment of Douglas-fir. Process Biochemistry, 49:466-473, 2014.

Figure 2:
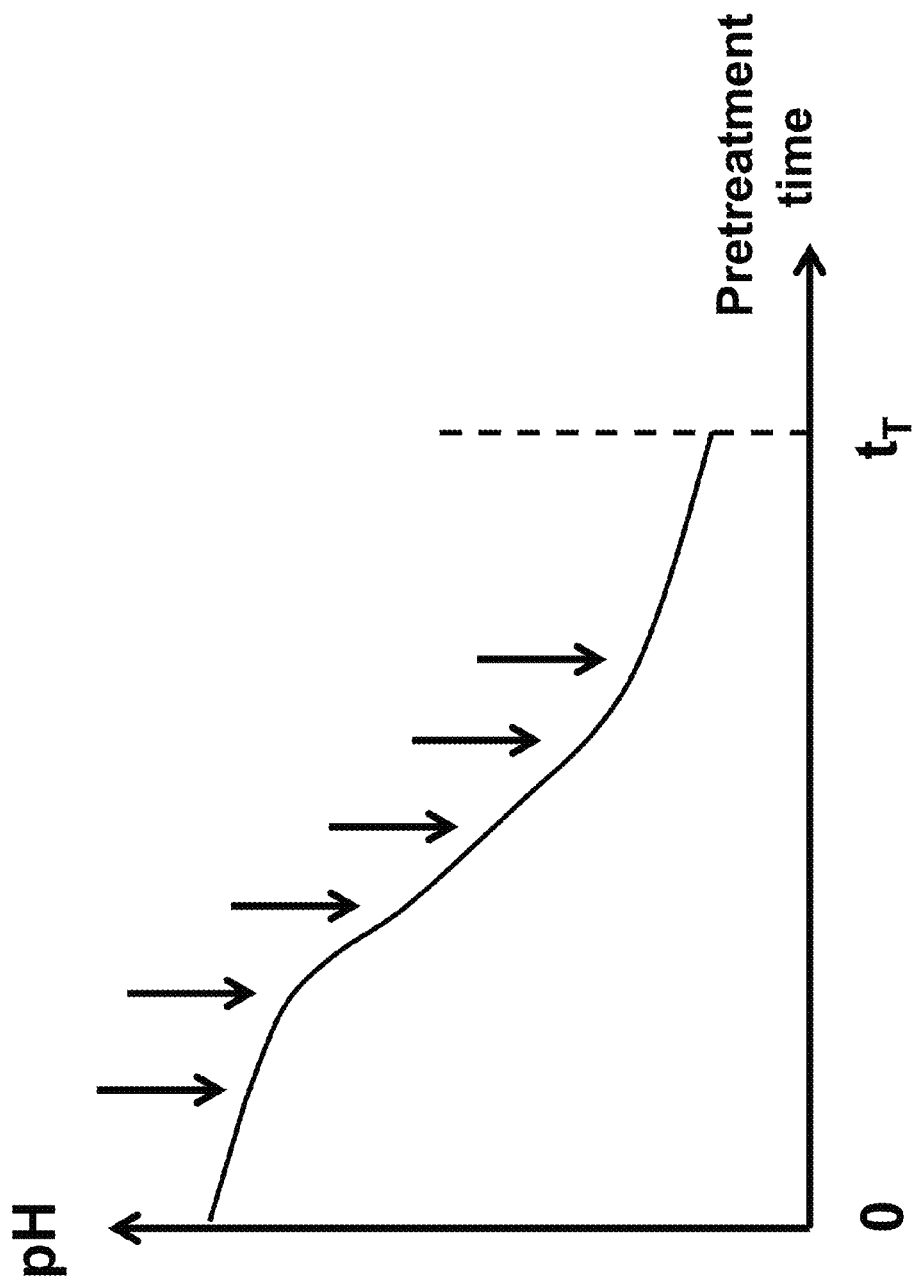
FIG. 2. A schematic diagram showing the time dependent pH profile through a continuous or multi-step pH adjustment.
Figure 3A:
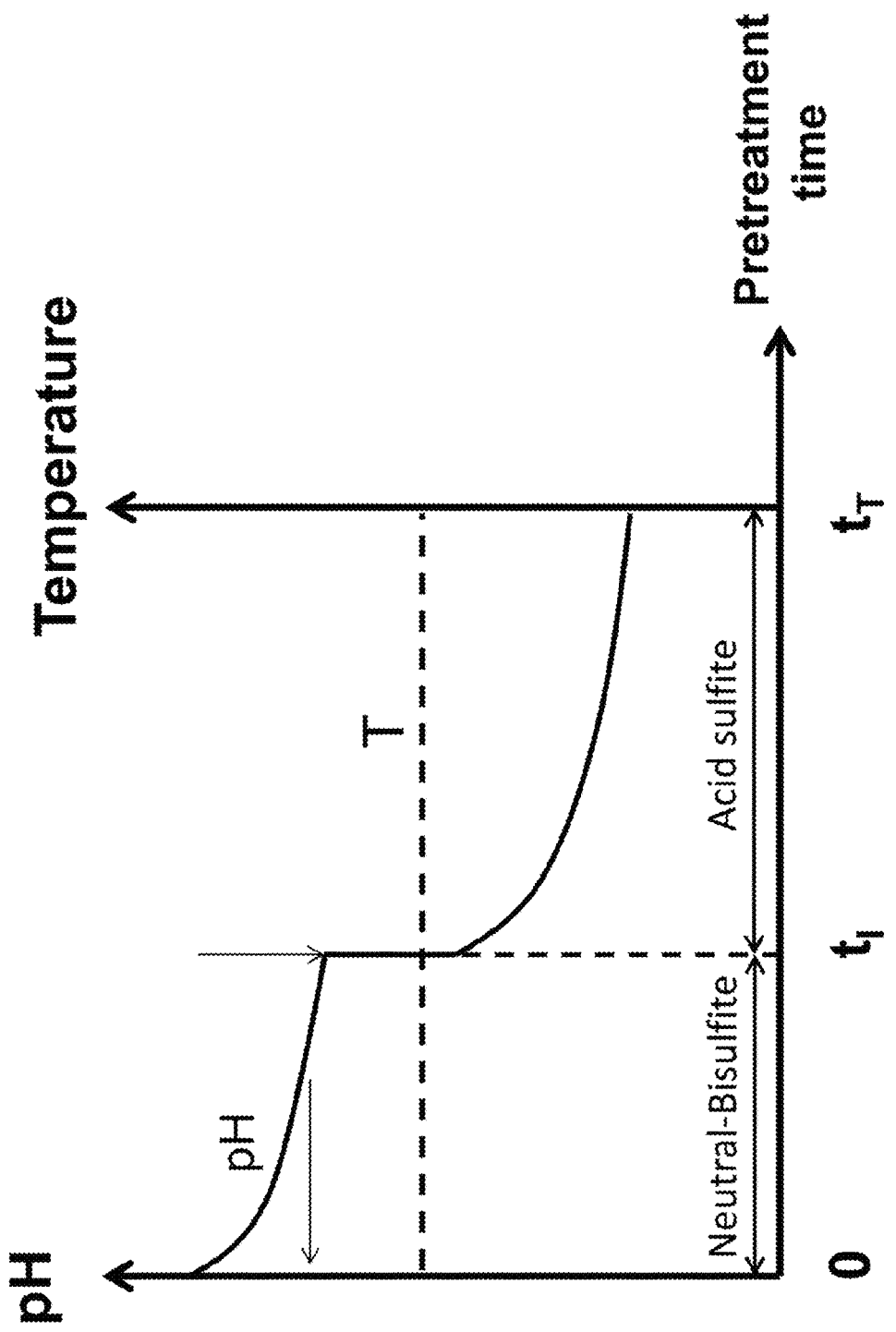
FIG. 3A. A schematic diagram showing the time dependent pH profile through a one point pH adjustment with constant temperature.

The first stage of the pretreatment ends upon the introduction of a pH-lowering agent into the reaction mixture. The introduction of the pH-lower agent can take place directly in the same reaction chamber in which the first stage of the pretreatment is carried out without washing or cooling the solids and/or removing the liquor. However, it is also possible to transfer the mixture into a second reaction chamber prior to carrying out the second stage of the pretreatment. Again, washing or cooling of the pretreated solids from the first stage is not needed, which is an advantage of the methods. Various agents may be used to lower the pH of the mixture. For example, sulfur dioxide can be injected into the solution. Alternatively, acids such as sulfuric acid can be injected. The introduction of pH-lowering agent reduces the pH of the reaction mixture to a value in the range from about 1 to less than 3. In some embodiment the pH is reduced to a value in the range from about 1.2 to about 2.0. The increased acidity of the reaction mixture promotes the dissolution of hemicelluloses, thereby improving the enzymatic digestibility of the pretreated biomass solids. The pH-lowering agent can be introduced in multiple doses (e.g., in a sequence of injections). This is illustrated schematically in the graph of pH versus pretreatment time ($t_T$) of FIG. 2, where the downward arrows represent sequential introductions of a pH-lowering agent, resulting in a gradual decrease in solution pH. Alternatively, as shown in FIG. 3A, the pH-lowering agent can be introduced in a single dose (at $t=t_{i1}$), resulting in an abrupt decrease in solution pH.

Figure 3B:
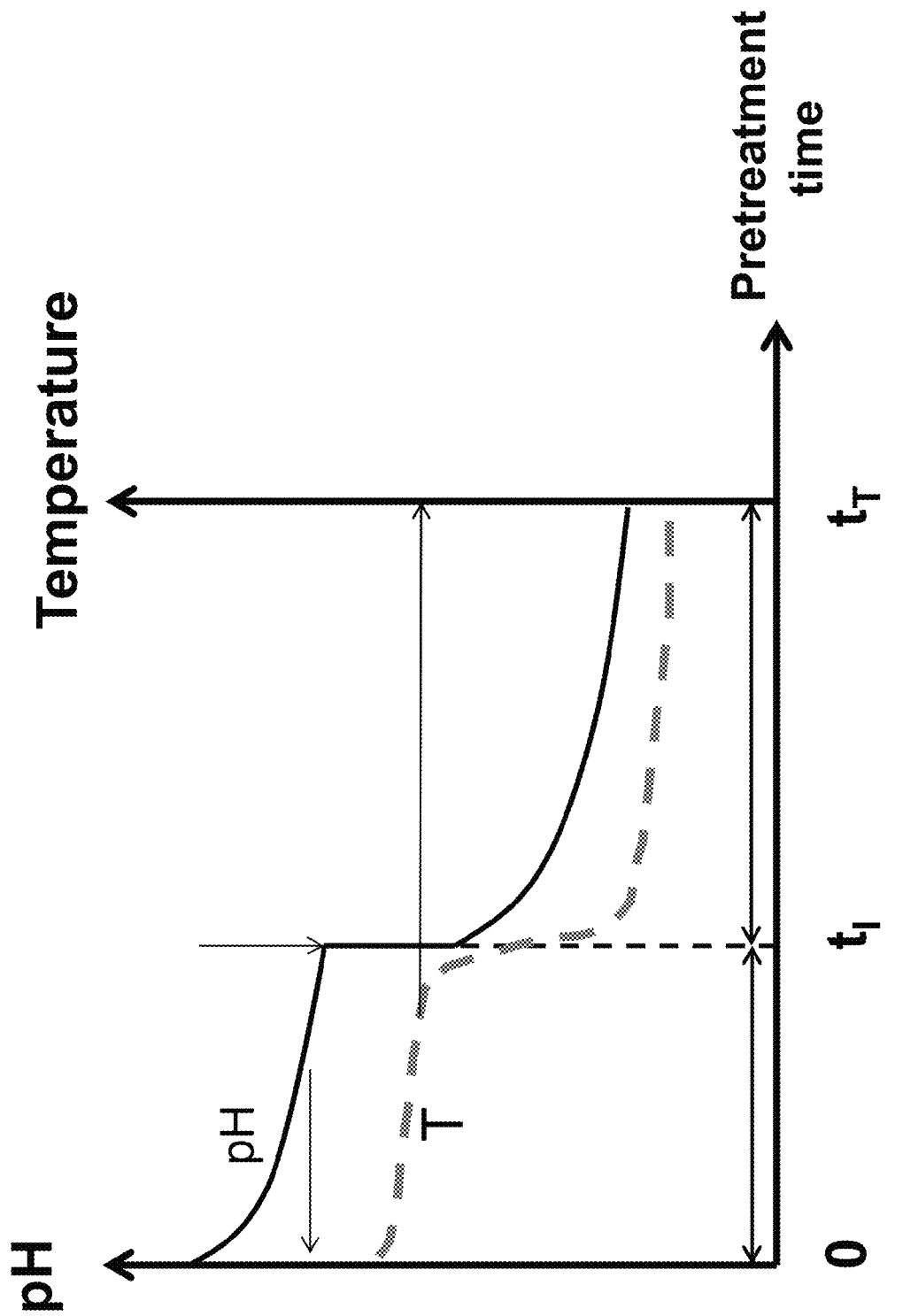
FIG. 3B. A schematic diagram showing the time dependent pH profile through a one point pH adjustment with temperature profiling.

During the second stage of the pretreatment, the mixture can be maintained in the same temperature range as that of the first stage—that is, from about 150° C. to about 200° C. However, in some embodiments, the temperature of the reaction mixture is decreased during the second pretreatment stage to reduce sugar degradation, as shown schematically in FIG. 3B.

The optimal duration of the second pretreatment period will depend on the first pretreatment reaction temperature and the total overall treatment time. Guidance for selecting an appropriate duration can be found in Zhang, Houtman, and Zhu, Using Low Temperature to Balance Enzymatic Saccharification and Furan Formation during SPORL Pretreatment of Douglas-fir. Process Biochemistry, 49:466-473, 2014. This guidance provides the total desired pretreatment duration of the control run without pH profiling using the following equation $$\frac{t^{T1}}{t^{T2}} = \exp\left[\frac{E}{R}\left(\frac{1}{T1} - \frac{1}{T2}\right)\right] \quad (1)$$

where E=100,000 J/mole is the activation energy and can be used for softwoods. R=8.314 J/mole/K is the universal gas constant. At T1=180° C., $t^{T1}$=30 min can be used for softwoods based on laboratory optimization (Zhou, Zhu et al., Bioconversion of beetle-killed lodgepole pine using SPORL: Process scale-up design, lignin coproduct, and high solids fermentation without detoxification. Ind. Eng Chem Res., 52:16057-16065, 2013). Then the total pretreatment time $t^{T2}$ at any T2 can be determined from Eq. (1). By way of illustration, in some embodiments presented here, $t^{T2}$=75 min using T2=165° C.

An increased temperature and pH in the first stage allow for improved delignification relative to a control run which has a lower pH and/or a lower temperature. Therefore, the duration of the first stage can be relatively short, for example less than half of the total time for the control run. The duration of the second period of pretreatment is the remaining time from the total pretreatment duration $t^{T2}$ calculated using eq. (1). By way of illustration, in some embodiments, the second pretreatment period can have a duration of 90 minutes or less. This includes durations of 70 minutes or less, 50 minutes or less, 30 minutes or less and 10 minutes or less.

The product of the pretreatment method comprises lignocellulosic biomass wet solids and a process liquor containing hydrolysates from the pretreatment. The lignocellulosic biomass solids are characterized in that they have a substantially lower hemicellulose content and, typically, a slightly lower lignin content than the starting lignocellulosic biomass. In some embodiments, the total amount of lignin removed from the lignocellulosic biomass by the pretreatment method is no greater than about 60%, based on weight. This includes embodiments in which the amount of lignin removed from the lignocellulosic biomass solids is no greater than about 50%, based on weight, and further includes embodiments in which the amount of lignin removed from in the lignocellulosic biomass solids is no greater than about 45%, based on weight.

The process liquor is characterized in that it contains relatively low quantities of cellulosic degradation products that inhibit enzymatic saccharification and/or fermentation and, therefore, limit bioethanol yield from pretreated materials. Examples of such degradation products include carbohydrate (e.g., sugar) degradation products such as furans, and further includes weak organic acids, such as acetic acid and formic acid. In some embodiments, the process liquor comprises no greater than about 6 g/L of degradation products when pretreatment is conducted using a liquor to biomass ratio of 3:1—equivalent to 18 g/kg of the lignocellulosic biomass starting material. This includes embodiments in which the process liquor comprises no greater than about 4 g/L of degradation products (or 12 g degradation products/kg lignocellulosic biomass). Moreover, the concentration of furans, such as furfural and 5-hydroxy-methyfurfural (HMF) can be particularly low. This is advantageous since furans can inhibit microbes for fermentation. By way of illustration, some embodiments of the pretreatment methods produce a process liquor comprising no greater than about 2 g/L of furans (or 6 g furans/kg of lignocellulosic biomass), which may be furfural, HMF or a combination of both. As used herein, the terms 'furan' or 'furans' refer to a class of compounds having a heterocyclic ring of four carbon atoms and one oxygen atom and includes HMF and furfural.

The product of the pretreatment method can be used as a feedstock for an enzymatic saccharification and fermentation process to convert lignocellulosic biomass into bioethanol. FIG. 1 is a schematic diagram of a system and apparatus that can be used for bioethanol production. In the conversion process the lignocellulosic biomass 102 is introduced into a reaction chamber 104 with steam heating. A sulfite solution is produced first in a separate reactor by bubbling $SO_2$ through hydroxide. The resulting solution 106 can then be introduced into chamber 104 through an input port. Reaction chamber 104 includes another input port to allow a pH-reducing agent 108 to be introduced into the chamber at the start of the second pretreatment stage. Pretreatment of lignocellulosic biomass 102 is conducted as described previously, and the product of the pretreatment 110 passes out of chamber 104 into a particle size reduction device 112 if the lignocellulosic starting material has a large particle size, such as a disk refiner. The pretreated biomass solids 114 and the process liquor 116 are then passed into an enzymatic saccharification and fermentation chamber 118. (Although the process depicted in this figure utilizes simultaneous enzymatic saccharification and combined fermentation, those processes can also be carried out separately.) During the enzymatic saccharification, multi-component cellulase enzymes that may include hemicellulases break down the carbohydrates in the biomass solids into monomeric sugars. The sugars are then consumed to produce ethanol via fermentation. Ethanol 120 can then be separated from the remaining fermentation products, such as lignosulfonates and waste water containing lignin residues, by distillation and/or purification.

The lignosulfonate, or the solubilized lignin, produced by the pretreatment may have a lower molecular weight distribution than those produced by sulfite pulping. For example, commercial lignosulfonate from sulfite pulping of softwoods typically has a MW of 40,000 Da, while lignosulfonate produced from the pretreatment methods describe here may have a MW of 20,000 or lower, as estimated from a previous study. (Zhou, Zhu et al., Bioconversion of beetle-killed lodgepole pine using SPORL: Process scale-up design, lignin co-product, and high solids fermentation without detoxification. Ind. Eng Chem Res., 52:16057-16065, 2013).

EXAMPLES

These examples illustrate effective sulfite pretreatment of lignocelluloses using pH profiling to significantly reduce the concentrations of furans and acetic acid, while achieving excellent enzymatic saccharification of the pretreated lignocelluloses. Pretreatments were conducted at mild acidic (bisulfite pH 3-5) to alkali (sulfite pH 10) levels for a period of time, followed by injection of sulfur dioxide ($SO_2$) or acid to acidify the pretreatment process liquor to a final pH of approximately 1.2-2.0 for effective dissolution of hemicelluloses. Best results were obtained using an initial pH between 3-5.

All demonstrations of the present methods were conducted according to the schematic flow diagram shown in FIG. 1 and the pH profiling schedule shown in FIG. 3A using a single injection of sulfuric acid at $t_i$. Although it is desirable to use $SO_2$ in the methods, for demonstrating the concept sulfuric acid was used as pH-reducing agent, as it was easier to practice in laboratory. The lignocellulosic biomass used was a softwood forest residue (denoted FS10 here). All pretreatments were conducted in a 23-L laboratory wood pulping digester heated using a steam jacket and rotated at 2 rpm for mixing. Pretreatment was conducted at 165° C. using dilute sulfite solution with sulfuric acid. The total pretreatment duration was fixed at $t_T$=75 min based on calculation using Eq. (1). After each pretreatment, the pretreated materials were disk-milled together with pretreatment spent liquor in a 12-inch disk refiner (Andritz Sprout-Bauer Atmospheric Refiner, Springfield, Ohio) using a pair of disk-plates with pattern of D2-B505. All disk-milling runs were conducted at 2,570 rpm with a disk plate gap of 1.0 mm.

Materials

Commercial cellulase enzymes Cellic® CTec3 (abbreviated CTec3) were generously provided by Novozymes North America (Franklinton, N.C., USA). The cellulase activity was 217 FPU/mL as calibrated by a literature method. (See, Wood T M, Bhat K M. 1988. Methods for measuring cellulase activities. Methods in enzymology 160:87-112.) Sodium acetate buffer, sulfuric acid, and sodium bisulfite were used as received from Sigma-Aldrich (St. Louis, Mo.). All chemicals were ACS reagent grade.

*Saccharomyces cerevisiae* YRH400 is an engineered fungal strain for xylose fermentation (Hector et al. 2011). The strain was grown at 30° C. for 2 days on YPD agar plates containing 10 g/L yeast extract, 20 g/L peptone, 20 g/L glucose, and 20 g/L agar. A colony from the plate was transferred by loop to liquid YPD medium in a flask and cultured overnight at 30° C. with agitation at 90 rpm on a shaking bed incubator (Thermo Fisher Scientific, Model 4450, Waltham, Mass.). The biomass concentration was monitored using optical density at 600 nm ($OD_{600}$) using a UV-Vis spectrometer (Model 8453, UV-visible spectroscopy system, Agilent Technologies, Palo Alto, Calif.). The cultured medium was used to inoculate the fermentation culture.

Enzymatic Hydrolysis

Enzymatic hydrolysis of the pretreated solid substrates was conducted at 2% (w/v) in 50 mL of 50 mM acetate buffer (pH 5.5) on a shake/incubator (Thermo Fisher Scientific, Model 4450, Waltham, Mass.) at 50° C. and 200 rpm. An elevated pH of 5.5, higher than the commonly used pH 4.8-5.0, can significantly reduce nonproductive cellulase binding to lignin leading to enhanced lignocellulose saccharification. (See, Lan T, Lou H, Zhu J. 2013a. Enzymatic saccharification of lignocelluloses should be conducted at elevated pH 5.2-6.2. BioEnergy Research:1-10; Lou H, Zhu J, Lan T Q, Lai H, Qiu X. 2013a. pH-Induced Lignin Surface Modification to Reduce Nonspecific Cellulase Binding and Enhance Enzymatic Saccharification of Lignocelluloses. ChemSusChem 6(5):919-927 and Wang Z, Lan T, Zhu J. 2013a. Lignosulfonate and elevated pH can enhance enzymatic saccarification of lignocelluloses. Biotechnology for Biofuels 6:9.) Either 5% (wt) NaOH or acetic acid was used to adjust the substrate suspension to pH 5.5. The CTec3 loading was 15 FPU/g glucan. Aliquots of 1 mL enzymatic hydrolysate were taken periodically for glucose analysis after centrifugation at 13000 g for 5 min. Each data point is the average of two analyses. The data from replicate runs were used to calculate the mean value and standard deviation that is used as error bars in some plots.

Quasi-Simultaneous Enzymatic Saccharification and Combined Fermentation (SSCombF)

Quasi-simultaneous enzymatic saccharification and combined fermentation (SSCombF) of the pretreated whole slurry was carried out in 250 mL Erlenmeyer flasks using a shaker/incubator (Thermo Fisher Scientific, Model 4450, Waltham, Mass.). The whole slurry (the complete mixture of pretreated solids and spent liquor) was adjusted to pH 6.2 with solid calcium hydroxide. Acetic acid/sodium acetate buffer (50 mM) of pH 6.0 was added into the pH adjusted mixture to conduct enzymatic hydrolysis using CTec3 at 18 FPU/g glucan. Two unwashed solids loadings of 18 and 21% were carried out. An elevated pH of 5.5, higher than the commonly used pH of 4.8-5.0, and lignosulfonate in the SPORL pretreatment liquor can significantly reduce nonproductive cellulase binding to lignin to enhance lignocellulose saccharification. (See, Lan T, Lou H, Zhu J. 2013a. Enzymatic saccharification of lignocelluloses should be conducted at elevated pH 5.2-6.2. BioEnergy Research:1-10; Lou H, Zhu J, Lan T Q, Lai H, Qiu X. 2013a. pH-Induced Lignin Surface Modification to Reduce Nonspecific Cellulase Binding and Enhance Enzymatic Saccharification of Lignocelluloses. ChemSusChem 6(5):919-927 and Wang Z, Lan T, Zhu J. 2013a. Lignosulfonate and elevated pH can enhance enzymatic saccharification of lignocelluloses. Biotechnology for Biofuels 6:9.) Liquefaction of the solid substrate was conducted at 50° C. and 200 rpm. The mixture was then cooled down to 35° C. and the shaker speed was reduced to 90 rpm and inoculated with 2 mL of yeast seed. The initial optical density of the yeast for all fermentation experiments was controlled at $OD_{600}$=5. No additional nutrients were applied during fermentation. Samples of the fermentation broth were taken periodically for analysis of monosaccharides, inhibitors and ethanol. Reported results are the average of duplicate analyses. Replicate fermentation runs were conducted to ensure experimental repeatability. The standard deviations were used as error bars in plotting.

Analytical Methods

The chemical compositions of the untreated and pretreated lignocelluloses were analyzed as described previously. (See, Luo X, Gleisner R, Tian S, Negron J, Zhu W, Horn E, Pan X, Zhu J. 2010. Evaluation of mountain beetle-infested lodgepole pine for cellulosic ethanol production by sulfite pretreatment to overcome recalcitrance of lignocellulose. Industrial & Engineering Chemistry Research 49(17):8258-8266.) All lignocellulosic samples were Wiley milled (Model No. 2, Arthur Thomas Co, Philadelphia, Pa., USA) to 20 mesh (~1 mm) and hydrolyzed in two stages using sulfuric acid of 72% (v/v) at 30° C. for 1 h and 3.6% (v/v) at 120° C. for 1 h. Carbohydrates of the hydrolysates were analyzed by high performance anion exchange chromatography with pulsed amperometric detection (ICS-5000, Dionex). Klason lignin (acid insoluble) was quantified gravimetrically. (See, Dence C W. 1992. The determination of lignin. In: Lin S Y, Dence C W, editors. Methods in lignin chemistry. Berlin: Springer-Verlag. p 33-61.) For fast analysis, glucose in the enzymatic hydrolysates was measured using a commercial glucose analyzer (YSI 2700S, YSI Inc., Yellow Springs, Ohio, USA).

Monosaccharides (glucose, mannose, xylose, arabinose, and galactose) in the enzymatic hydrolysates and fermentation broths were determined using a Dionex HPLC system (Ultimate 3000) equipped with an RI (RI-101) and UV (VWD-3400RS) detector and BioRad Aminex HPX-87P column (300×7.8 mm) operated at 80° C. Double distilled water (d.d.w.) was used as eluent at a flow of 0.6 mL/min. Inhibitor (acetic acid, furfural and hydroxymethyl furfural (HMF)) and ethanol were measured by the same HPLC system equipped with BioRad Aminex HPX-87H column (300×7.8 mm) operated at 60° C. Dilute sulfuric acid solution of 5 mM was used as eluent at a flow rate of 0.6 mL/min. All sample injection volumes were 20 μL. Samples were diluted in deionized water, and filtrated by a 0.22 μm filter prior to injection.

Example 1

Forest Residue of Douglas-Fir(FS-10)—Initial pH of 4.0

The Forest Residue

Forest residue is an affordable biomass feedstock for biofuel production. It can be sustainably produced in large quantities in North America and various regions of the globe. (See, Gan J, Smith C T. 2006. Availability of logging residues and potential for electricity production and carbon displacement in the USA. Biomass and Bioenergy 30(12):1011-1020; Kirschbaum MUF. 2003. To sink or burn? A discussion of the potential contributions of forests to greenhouse gas balances through storing carbon or providing biofuels. Biomass and Bioenergy 24(4-5):297-310 and Perlack R D, Stokes B J. 2011. DOE. 2011. U.S. Billion-Ton Update: Biomass Supply for a Bioenergy and Bioproducts Industry. Oak Ridge: Oakridge National Laboratory.) Forest residues have relatively high bulk densities and can be harvested year round which reduces on-site storage requirements, both of which are significant advantages over agriculture residues and herbaceous biomass and improve the supply chain logistics and reduce transportation costs. (See, Stephen J D, Mabee W E, Saddler J N. 2010. Biomass logistics as a determinant of second-generation biofuel facility scale, location, and technology selection. Biofpr 4:503-518 and Zhu J Y, Zhuang X S. 2012. Conceptual net energy output for biofuel production from lignocellulosic biomass through biorefining. Progress in Energy and Combustion Science 38(4):583-589.) However, forest residues, especially those from softwood species, such as the FS10 used in this example, are very recalcitrant to biochemical conversion through the biorefinery concept because bark and juvenile wood in the residues have high lignin content. A more severe pretreatment is often required to achieve desired saccharification but produces high levels of furans, inhibitive to downstream fermentation and conversion. Therefore, demonstrating efficient enzymatic saccharification with very low production of furans and acetic acid has significant importance.

Douglas-fir forest residues FS10 used in this example was collected from roadside piles resulting from a regeneration harvest in a Douglas-fir stand on Mosby Creek owned by Weyerhaeuser Company southeast of Cottage Grove in Lane County, Oreg. The residues were ground using a Peterson horizontal drum fixed-hammer grinder (4710 Horizontal Grinder) using a combination of 76 and 102 mm grates. The harvested residues were shipped to Weyerhaeuser Company at Federal Way, Wash. The moisture content was 43.9% measured at arrival. The collected residues were screened using a gyratory screen (Black-Clawson) equipped with a 1.75-inch diameter round-hole punched-plate top deck to remove oversized particles and a ⅛-inch clear-opening woven wire bottom screen (6 wires/inch mesh) to remove fines. The screen reject fines were 7.6%. The oversized particles were hammer milled at West Salem Machinery (Salem, Oreg.), which resulted in near zero oversized particles and 14.9% fines of the 7.6% initial screen oversize particles. The total rejection of fines was therefore at 9% with near zero rejection of oversize particles. The accept residue, FS10, was then air-dried to a moisture content of 15% and shipped to the USDA Forest Products Laboratory, Madison, Wis. The chemical composition of FS10 is listed in TABLE I.

TABLE I

Chemical composition of untreated and treated FS10 solids.

| Run Label | K Lignin (%) | Arabinan[1] (%) | Galactan (%) | Glucan (%) | Xylan (%) | Mannan (%) | Solids yield (%) |
| --- | --- | --- | --- | --- | --- | --- | --- |
| Untreated | 29.30 | 1.04 | 2.00 | 40.97 | 5.70 | 9.67 | 100 |
| Initial Pretreatment pH = 4.0 | | | | | | | |
| t0A4B12 | 27.85 | ND | 0.23 | 63.39 | 2.23 | 2.58 | 61.27 |
| t25A4B12 | 21.54 | ND | 0.17 | 67.16 | 3.75 | 3.93 | 60.39 |
| t35A4B12 | 21.40 | ND | 0.17 | 66.62 | 3.31 | 3.54 | 61.65 |
| t45A4B12 | 22.13 | ND | 0.30 | 62.31 | 3.37 | 4.12 | 62.23 |

TABLE I-continued

Chemical composition of untreated and treated FS10 solids.

| Run Label | K Lignin (%) | Arabinan[1] (%) | Galactan (%) | Glucan (%) | Xylan (%) | Mannan (%) | Solids yield (%) |
|---|---|---|---|---|---|---|---|
| Initial Pretreatment pH = 10.0 | | | | | | | |
| t0A14S15 | 33.21 | ND | ND | 54.74 | 2.26 | 2.47 | 58.64 |
| t25A14S15 | 25.46 | 0.15 | 1.57 | 49.46 | 4.21 | 10.39 | 60.25 |
| t45A14S15 | 24.30 | 0.30 | 1.84 | 49.70 | 4.57 | 11.07 | 64.00 |

[1]ND stands for undetectable.

pH Profiling Pretreatment—Initial pH=4.0

Four pretreatments were conducted at 165° C. with one control, i.e, no active pH profiling, and three active pH profiling runs. In commercial practice, sulfite pretreatment will be conducted using $SO_2$ bubbling through a hydroxide solution to produce a sulfite solution of desired pH. Using pH profiling pretreatment, the amount of $SO_2$ applied initially should be based on the desired initial pH whether in a neutral/near neutral (for example, pH=6-8) or bisulfite range (pH=3-5) and the base of the bisulfite. The amount of hydroxide applied is based on a desired loading of bisulfite on oven dry wood base, for example 2, 4, 6, 10, 12, 14%. To practice the process described in FIG. 3A, additional $SO_2$ need to be injected during pretreatment at time $t_i$. In the laboratory, one can simply use either sodium bisulfite (pH=4.0) or sodium sulfite (pH=10) with the injection of sulfuric acid to practice the process in FIG. 3A. In this example, the control run uses sodium bisulfite together with sulfuric acid applied initially ($t_i$=0) to a desired initial pH of approximately 2.0 when measured at room temperature (23° C.). No additional acid was applied. For pH profiling runs, the same amount of sodium bisulfite was applied at the beginning of pretreatment without the application of acid. The same amount of sulfuric acid as that used in the control run was applied through injection to the digester at different times $t_i$ during pretreatment. The total chemical loadings, sodium bisulfite (B) and sulfuric acid (A) on oven dry wood base, total pretreatment duration $t_T$, temperature, and liquid to wood ratio (L/W) in the pH profiling runs were identical to those used in the control run, so that fair comparisons can be made to demonstrate the advantages of the pH profiling concept. The pretreatment conditions are listed in TABLE II.

liquors) are listed in Table IIIA and IIIB, which are shown in FIG. 19 for the control and pH profiling pretreatments. As expected, the pH profiling runs increased delignification, i.e., lignin yield in washed solids was reduced from 17% for the control run to approximately 13% for the pH profiling runs. pH profiling decreased hemicellulose removal to result in more xylan and mannan in washed solids, i.e., approximately 2.1% and 2.4%, respectively, in comparison with 1.4% and 1.6% for the control run. pH profiling also slightly increased glucan yield from the washed solids which resulted in a lower glucose yield in the spent liquor. The increased carbohydrate yields in the solid substrates facilitated increased monomeric sugar recovery through enzymatic saccharification, which is beneficial to increasing overall sugar yield. pH profiling also reduced monomeric xylose and mannose yields in the spent liquor. It is expected that a significant amount of dissolved xylan and mannan are present in the form of olig-xylose and olig-mannose, respectively. The reduction of furan formation by pH profiling is very obvious as shown in the tables of FIG. 19.

Figure 4:
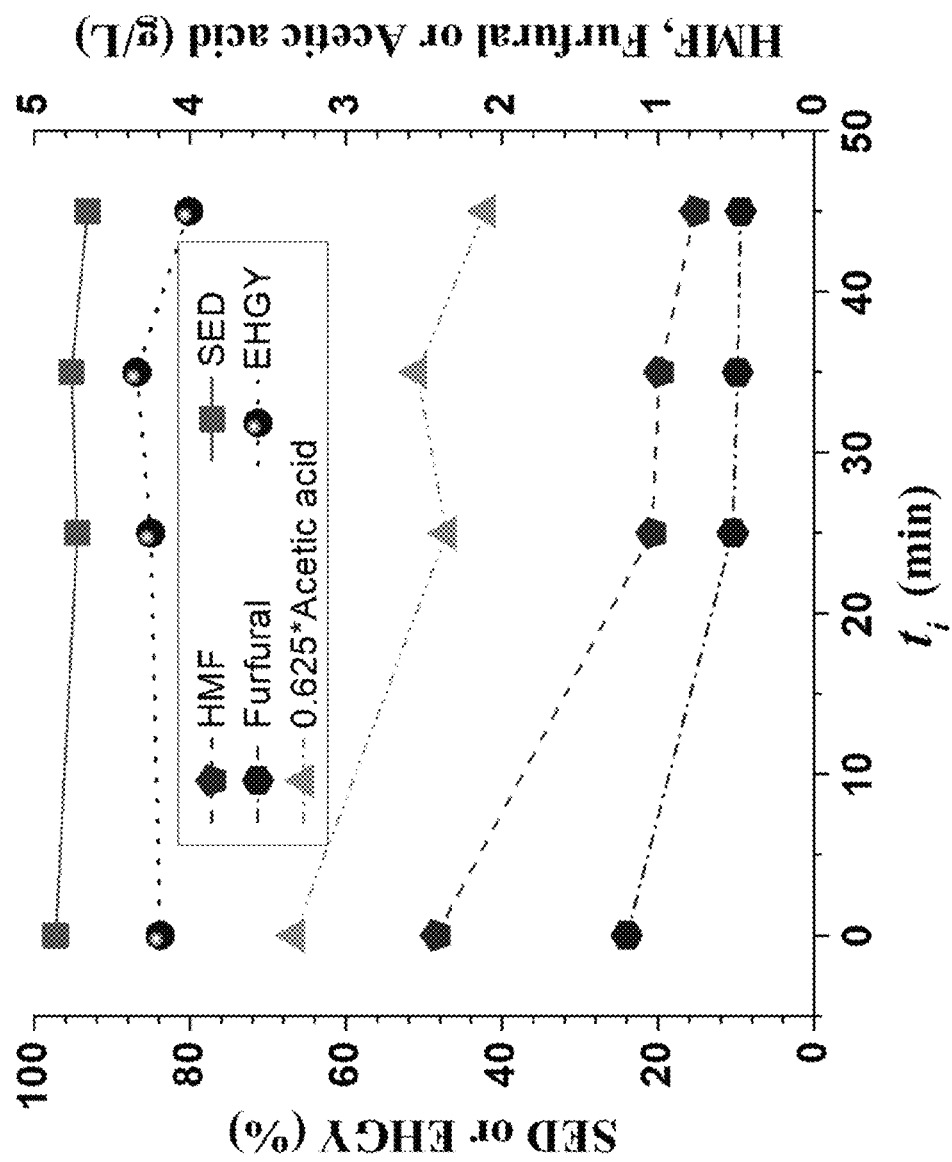
FIG. 4. Effect of acid injection time for pH profiling in a sulfite (SPORL) pretreatment on enzymatic saccharification expressed by substrate enzymatic digestibility (SED) and enzymatic hydrolysis glucose yield (EHGY), as well as 5-hydroxymethyl furfural (HMF), furfural, and acetic acid formation.

Effects of pH Profiling on Furan and Acetic Acid Formation and Cellulose Saccharification To further illustrate the effectiveness of pH profiling for reducing furan and acetic acid formation, the HMF, furfural and acetic acid concentration in the pretreatment spent liquor was plotted against the acid injection time $t_i$ as shown in FIG. 4. HMF, furfural, and acetic acid concentrations were reduced from approximately 2.5, 1.2, and 5.3 g/L, respectively, for the control run to approximately 0.8, 0.5, and 3.5 g/L, or by approximately 70, 60, and 35% when using the pH profiling

TABLE II

List of pretreatment conditions of FS10 at 165° C.

| Run Label | $t_T$ (min) | Initial pH | A at t = 0 (wt %) | Sulfite at t = 0 (wt %) | $t_i$ (min) | A at $t_i$ (wt %) | Final pH | L/W |
|---|---|---|---|---|---|---|---|---|
| Initial Pretreatment pH = 4.0 | | | | | | | | |
| t0A4B12 | 75 | 1.79 | 2.2 | 12 | 0 | 0 | 1.45 | 3 |
| t25A4B12 | 75 | 4.06 | 0 | 12 | 25 | 2.2 | 1.72 | 3 |
| t35A4B12 | 75 | 4.06 | 0 | 12 | 35 | 2.2 | 1.40 | 3 |
| t45A4B12 | 75 | 4.06 | 0 | 12 | 45 | 2.2 | 1.66 | 3 |
| Initial Pretreatment pH = 10.0 | | | | | | | | |
| t0A14S15 | 75 | 2.07 | 7.9 | 14.5 | 0 | 0 | 1.64 | 3 |
| t25A14S15 | 75 | 10.0 | 0 | 14.5 | 25 | 7.9 | 3.97 | 3 |
| t45A14S15 | 75 | 10.0 | 0 | 14.5 | 45 | 7.9 | 4.48 | 3 |

Component Mass Balance of Pretreatments

The key wood component yields from the untreated, pretreated washed solids and pretreatment hydrolysates (spent technique. The results also suggest that injection time $t_i$ did not significantly affect the reductions in furan and acetic acid formation for the studied $t_i$ range of 25 to 45 min.

Figure 5:
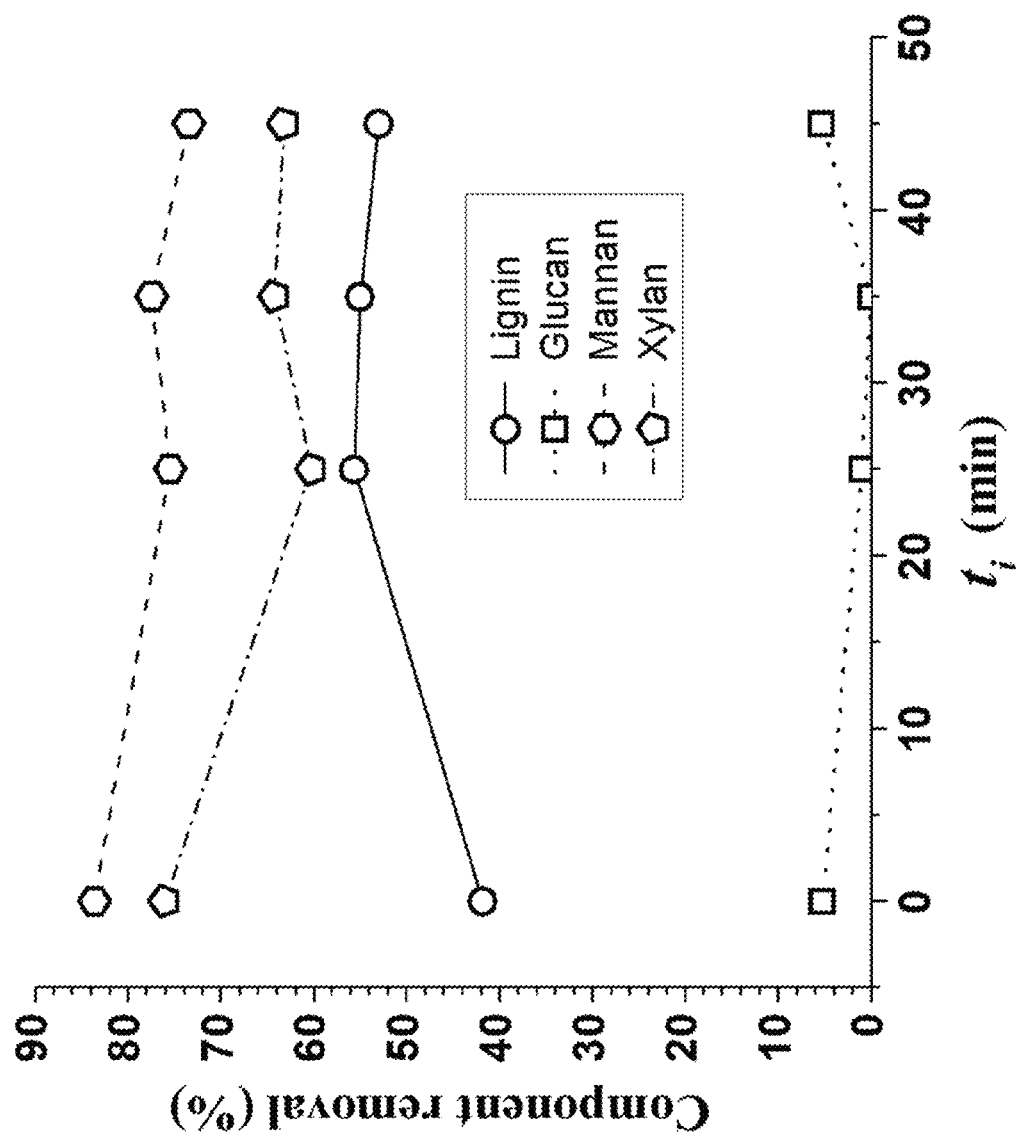
FIG. 5. Effect of acid injection time on delignification, glucan loss, and removal of xylan and mannan for pH profiling in a sulfite (SPORL) pretreatment.
Figure 6:
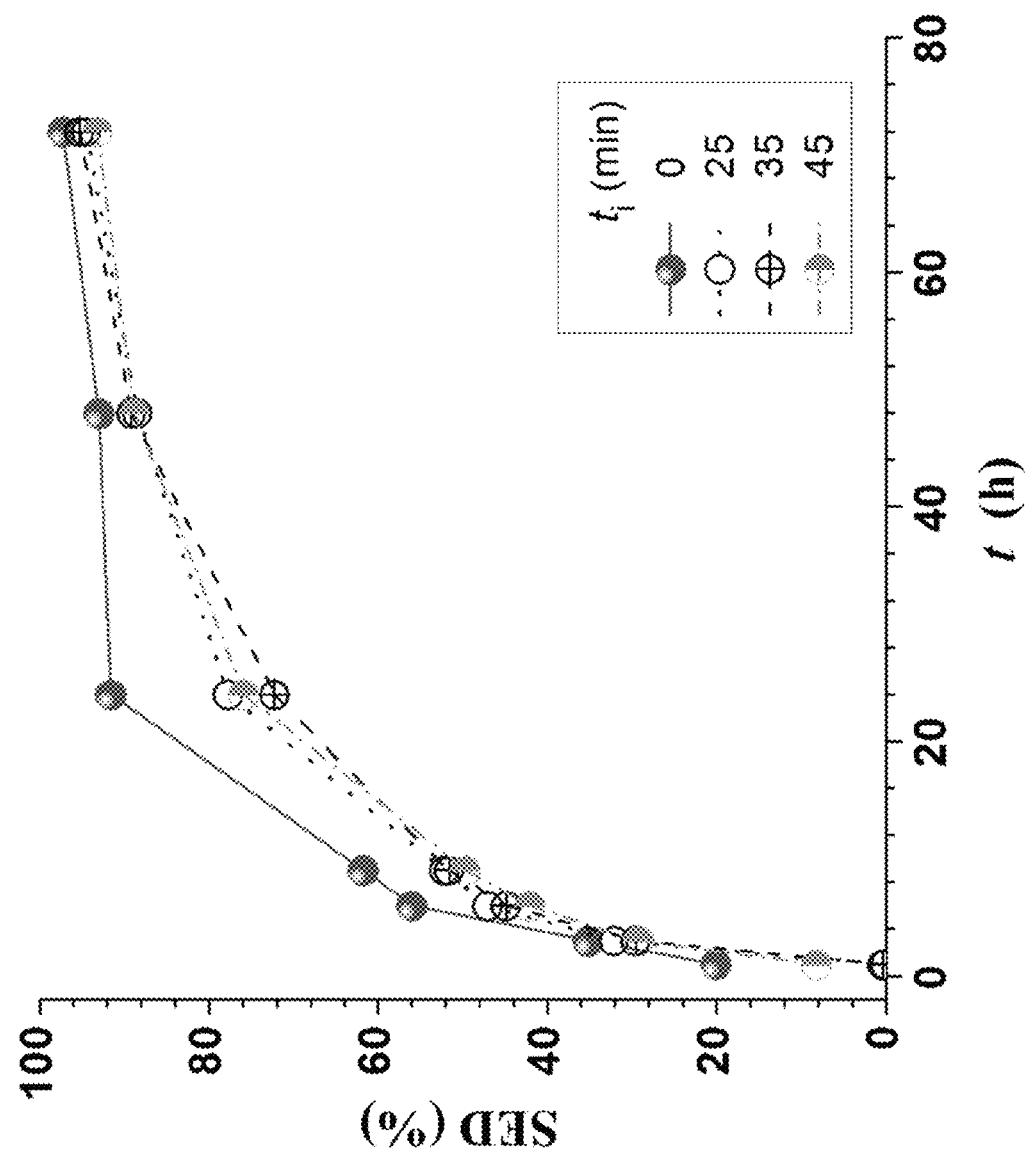
FIG. 6. Comparisons of time-dependent enzymatic saccharification expressed by substrate enzymatic digestibility (SED) using SPORL pretreated Douglas-fir forest residue (FS10) with different pH profiles in pretreatment.

To examine the effects of pH profiling on cellulose saccharification, substrate enzymatic digestibility (SED), defined as the percentage of substrate glucan enzymatically saccharified to glucose, and enzymatic hydrolysis glucose yield (EHGY), defined as the percentage of wood glucan recovered as glucose through enzymatic hydrolysis alone, were also plotted against $t_i$ in FIG. 4. It appears that SED was not negatively affected by pH profiling. The results suggest that improved delignification in the pH profiling runs compensated for the reduced hemicellulose removal (FIG. 5 and FIG. 19) to achieve similar SED. Similarly, EHGY was not affected by pH profiling. The increased glucan recovery in the solid substrate as discussed previously (FIG. 19) compensated for the slight reduction in SED by pH profiling to maintain the same level of EHGY. The time dependent SED data showed that pH profiling reduced the rate of saccharification, but the final saccharification efficiency after 72 h was the same as that of the control run as shown in FIG. 6.

Comparison of Ethanol Production Between Control and pH Profile Pretreatments

Figure 7:
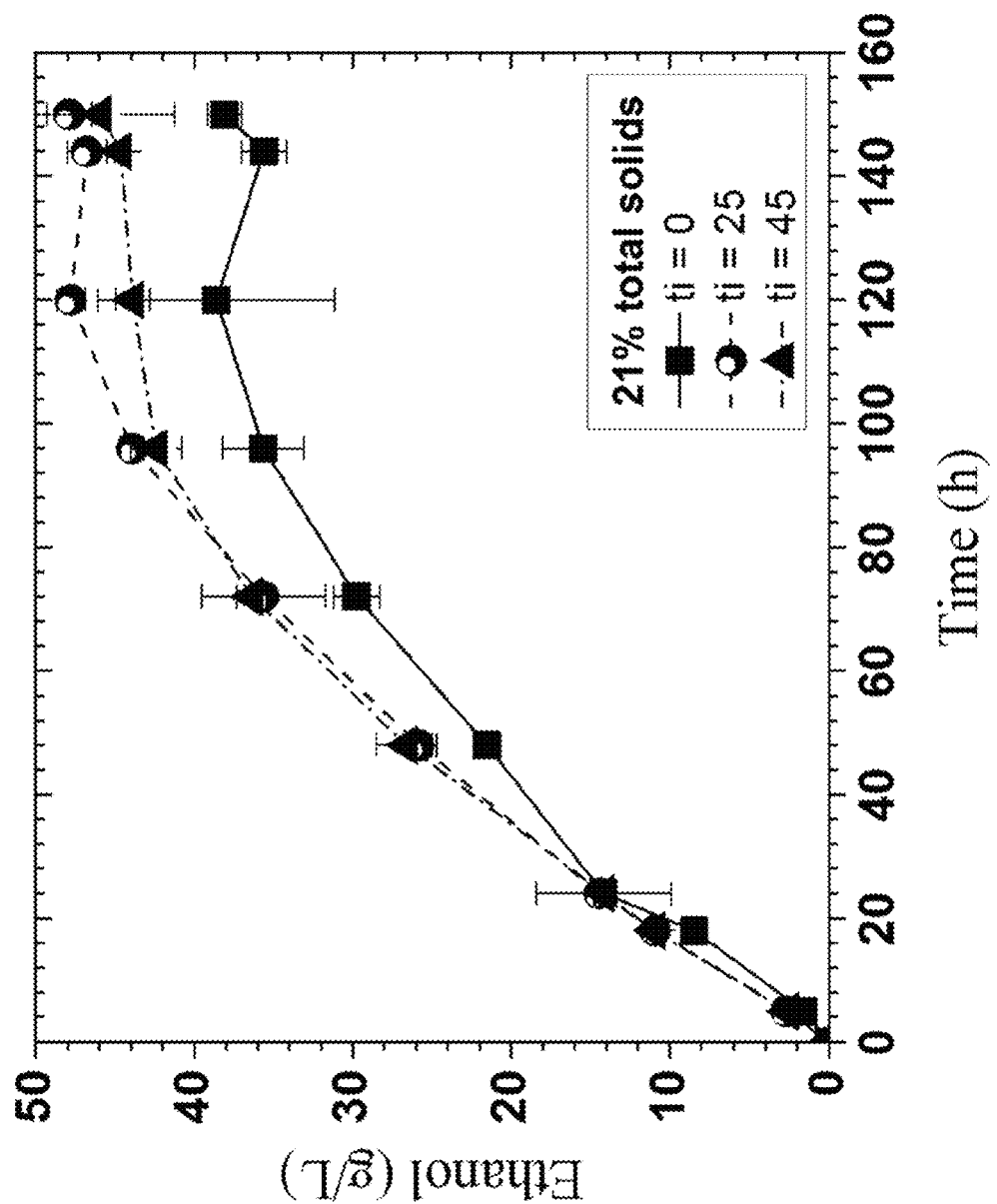
FIG. 7. Time-dependent ethanol production in fermentation at total solids loading of 21% using SPORL pretreated whole slurry Douglas-fir forest residue (FS10): Comparisons between pH profiling SPORL pretreatments with acid injection delay time $t_i$=25 and 45 min with the control pretreatment with $t_i$=0.
Figure 8:
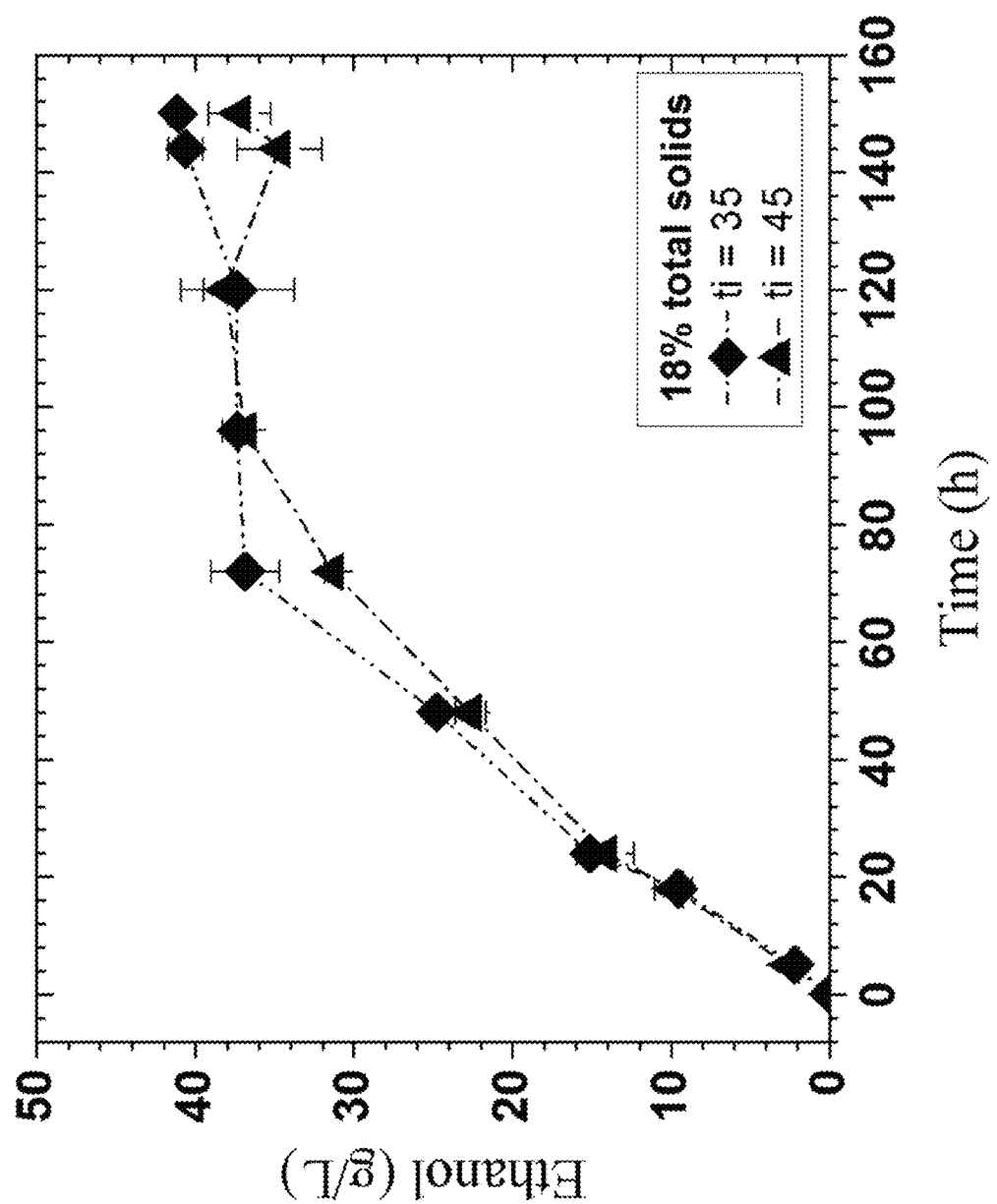
FIG. 8. Time-dependent ethanol production in fermentation at total solids loading of 18% using SPORL pretreated whole slurry Douglas-fir forest residue (FS10): Comparisons between two pH profiling SPORL pretreatments with acid injection delay time $t_i$=35 and 45 min respectively.
Figure 9:
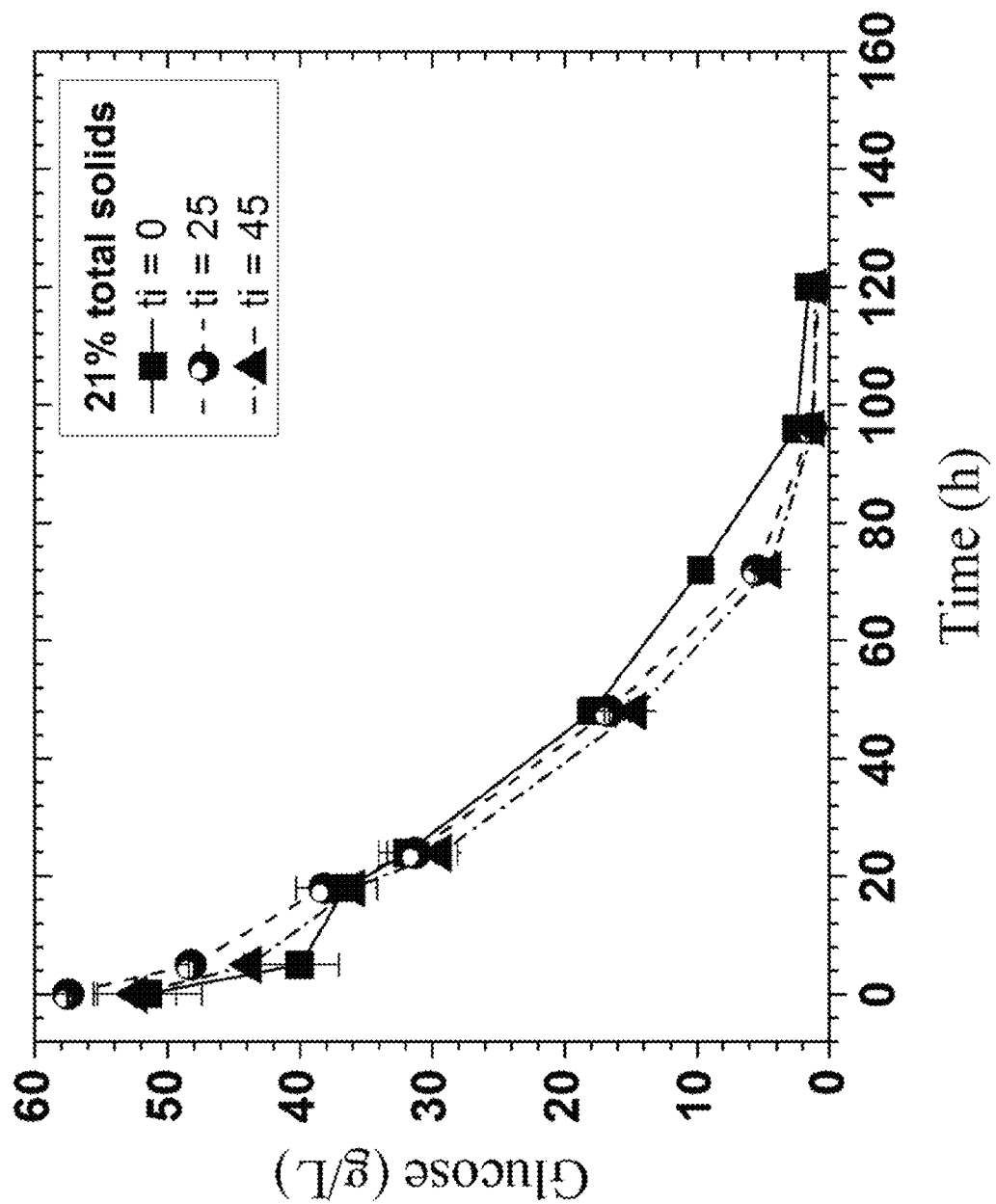
FIG. 9 Time-dependent glucose consumption in fermentation at total solids loading of 21% using SPORL pretreated whole slurry Douglas-fir forest residue (FS10): Comparisons between pH profiling SPORL pretreatments with acid injection delay time $t_i$=25 and 45 min with the control pretreatment with $t_i$=0.
Figure 10:
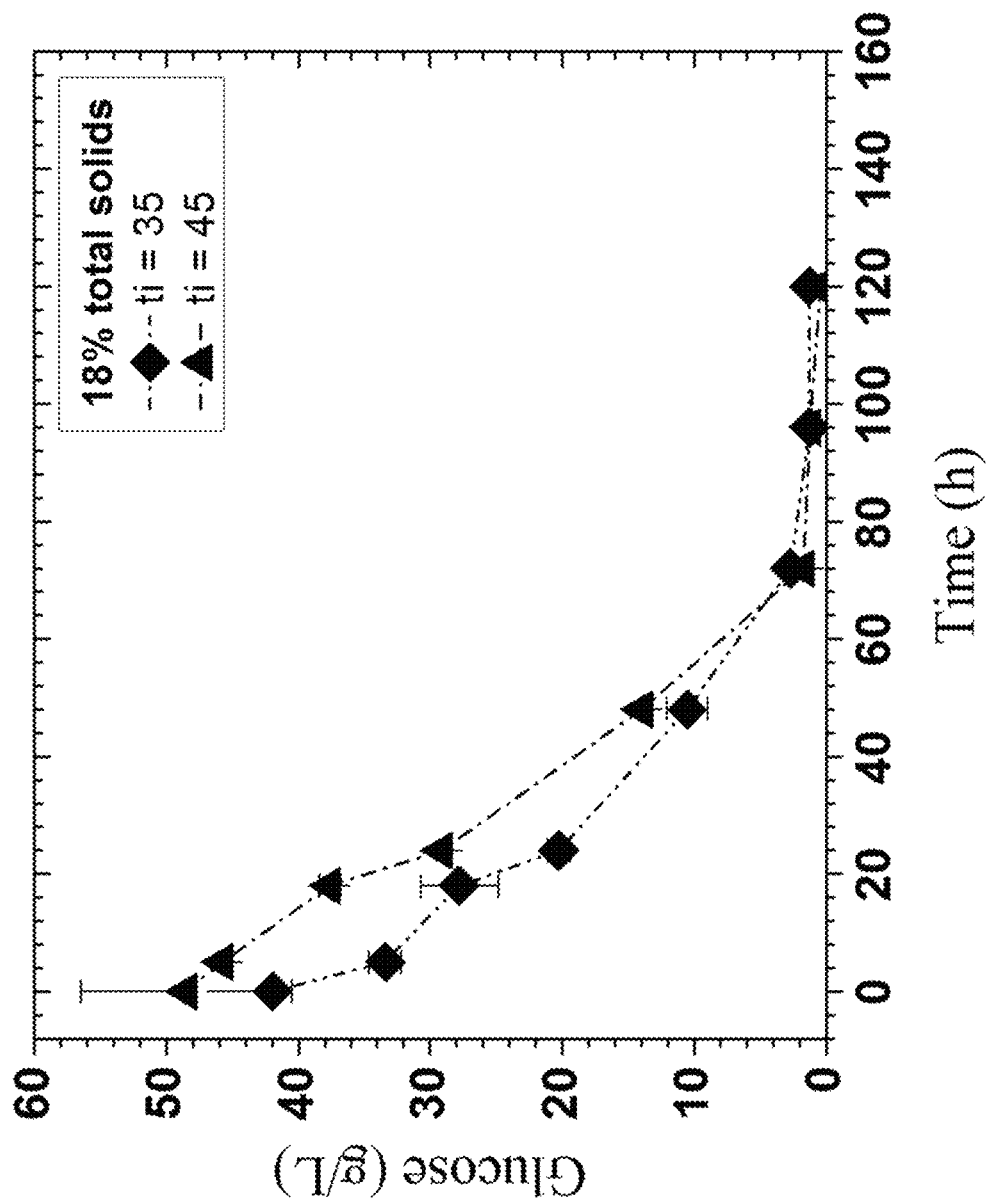
FIG. 10. Time-dependent glucose consumption in fermentation at total solids loading of 18% using SPORL pretreated whole slurry Douglas-fir forest residue (FS10): Comparisons between two pH profiling SPORL pretreatments with acid injection delay time $t_i$=35 and 45 min respectively.
Figure 11:
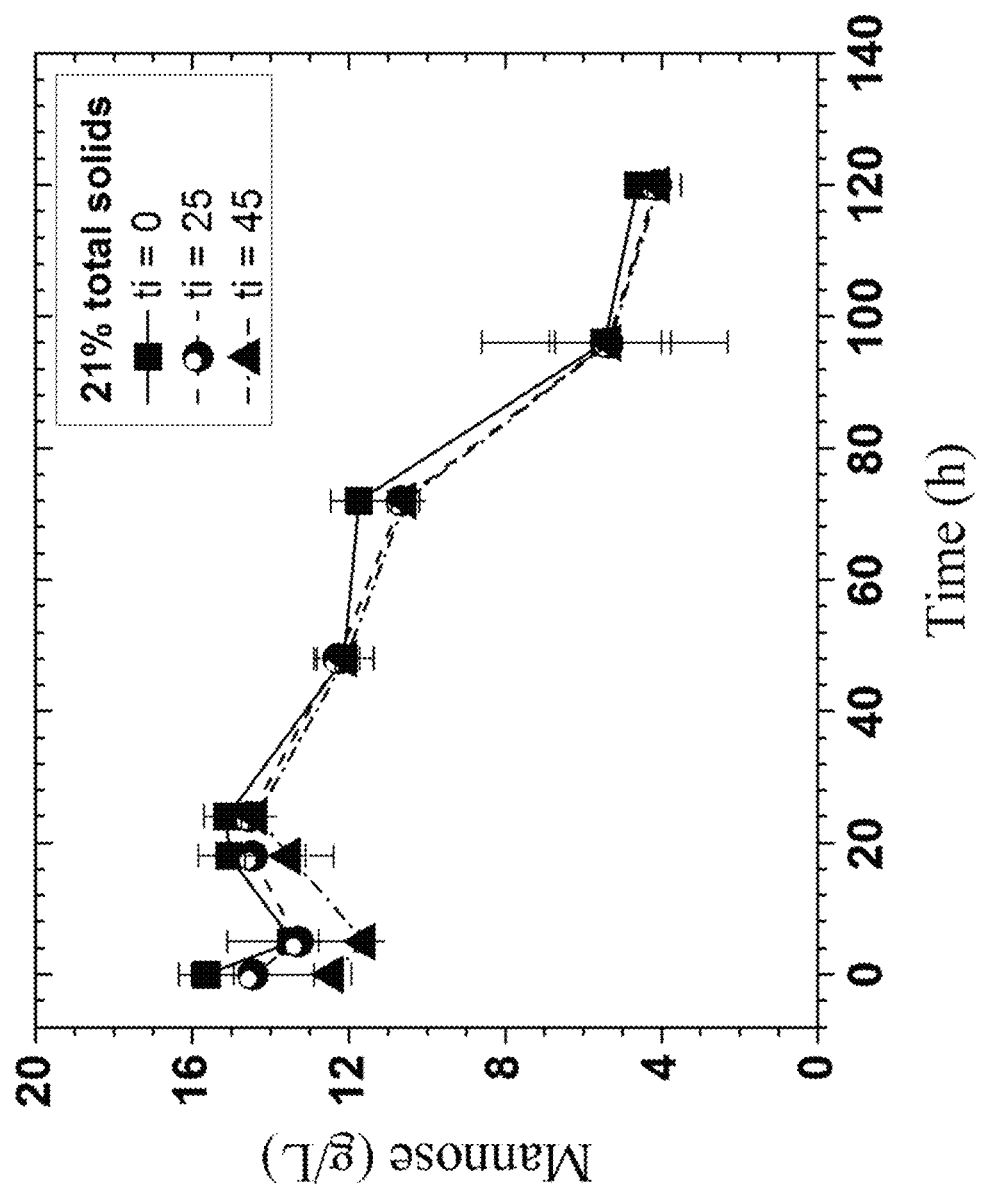
FIG. 11. Time-dependent mannose consumption in fermentation at total solids loading of 21% using SPORL pretreated whole slurry Douglas-fir forest residue (FS10): Comparisons between pH profiling SPORL pretreatments with acid injection delay time $t_i$=25 and 45 min with the control pretreatment with $t_i$=0.
Figure 12:
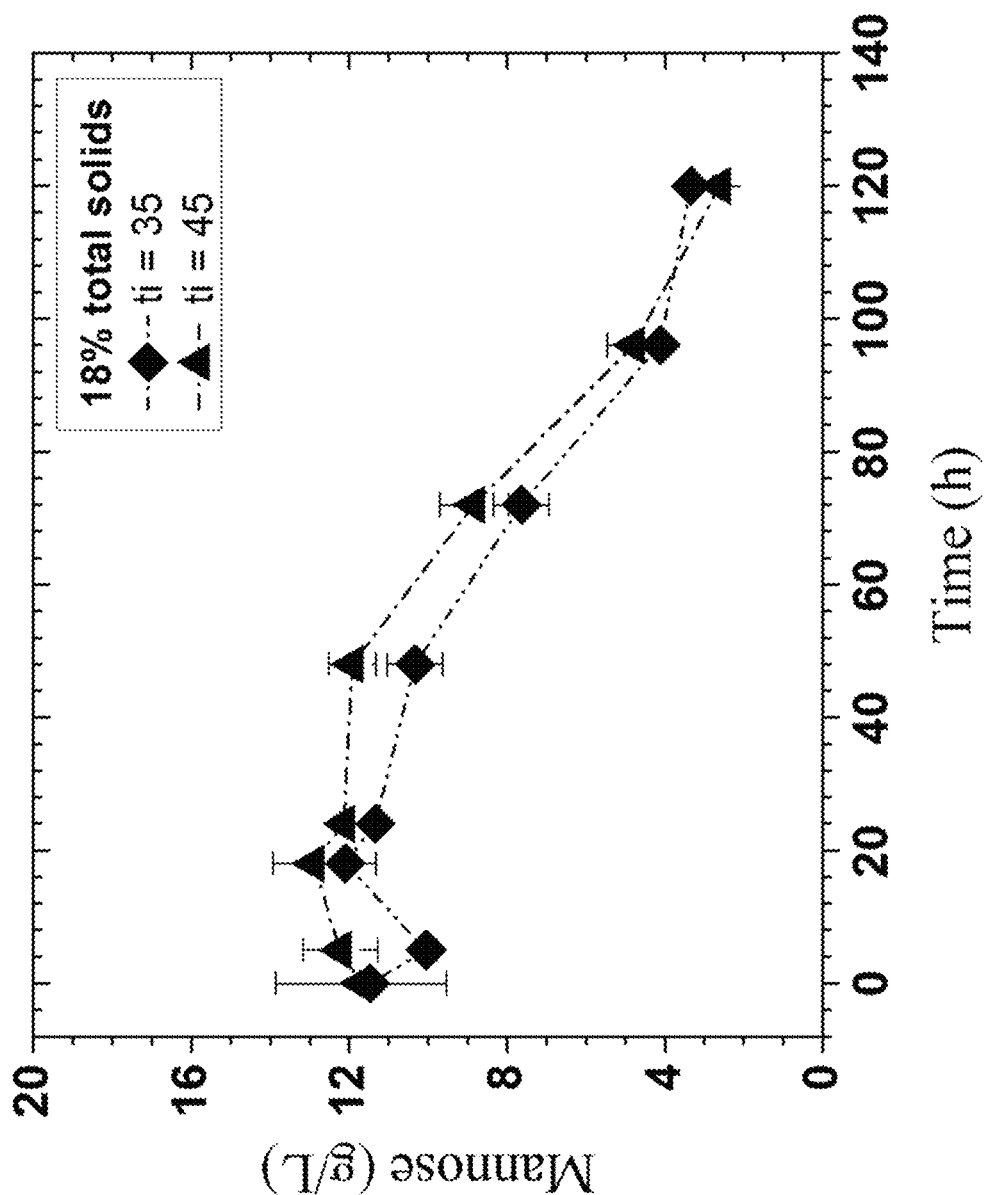
FIG. 12. Time-dependent mannose consumption in fermentation at total solids loading of 18% using SPORL pretreated whole slurry Douglas-fir forest residue (FS10): Comparisons between two pH profiling SPORL pretreatments with acid injection delay time $t_i$=35 and 45 min respectively.
Figure 13:
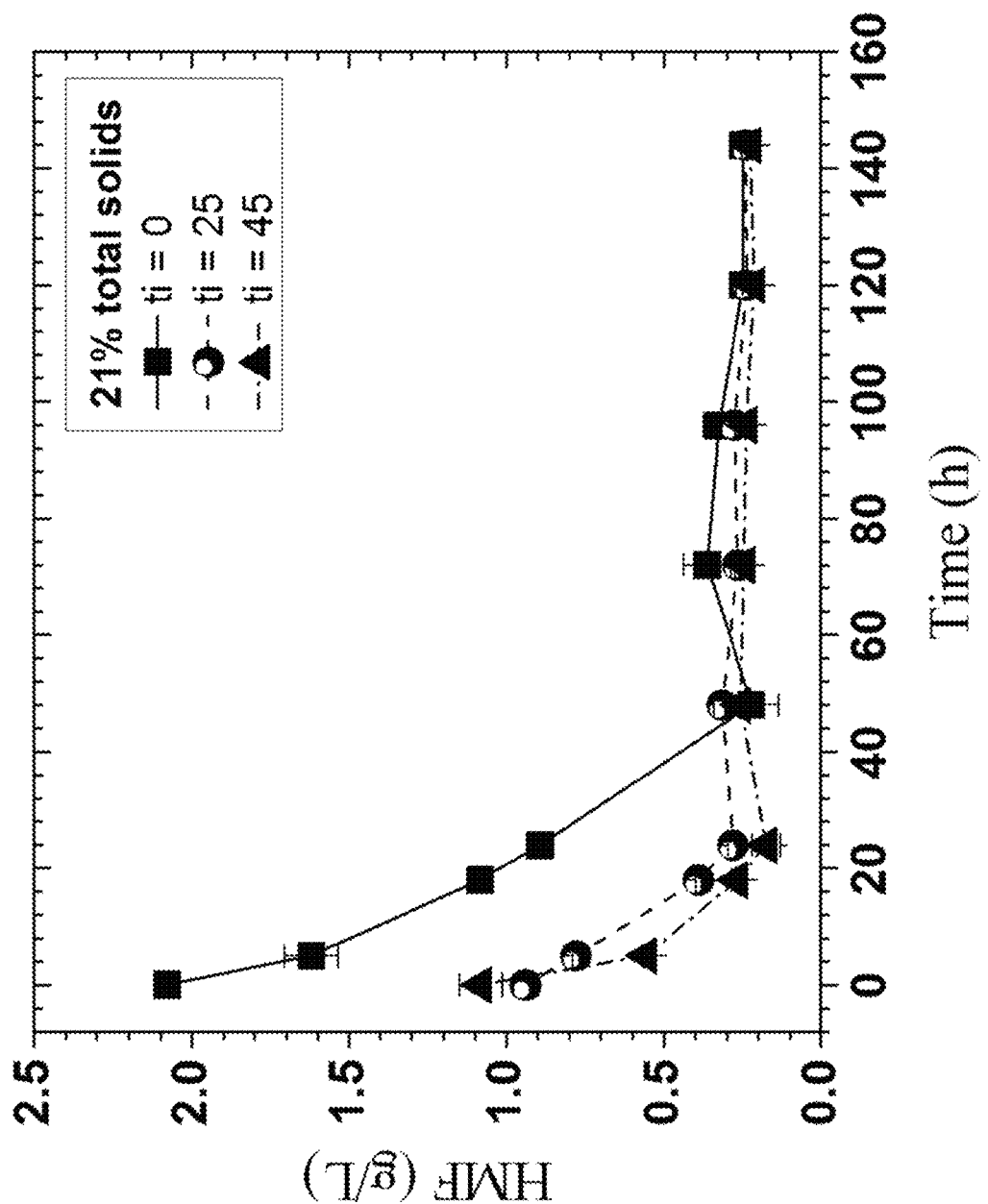
FIG. 13. Time-dependent HMF metabolization in fermentation at total solids loading of 21% using SPORL pretreated whole slurry Douglas-fir forest residue (FS10): Comparisons between pH profiling SPORL pretreatments with acid injection delay time $t_i$=25 and 45 min with the control pretreatment with $t_i$=0.
Figure 14:
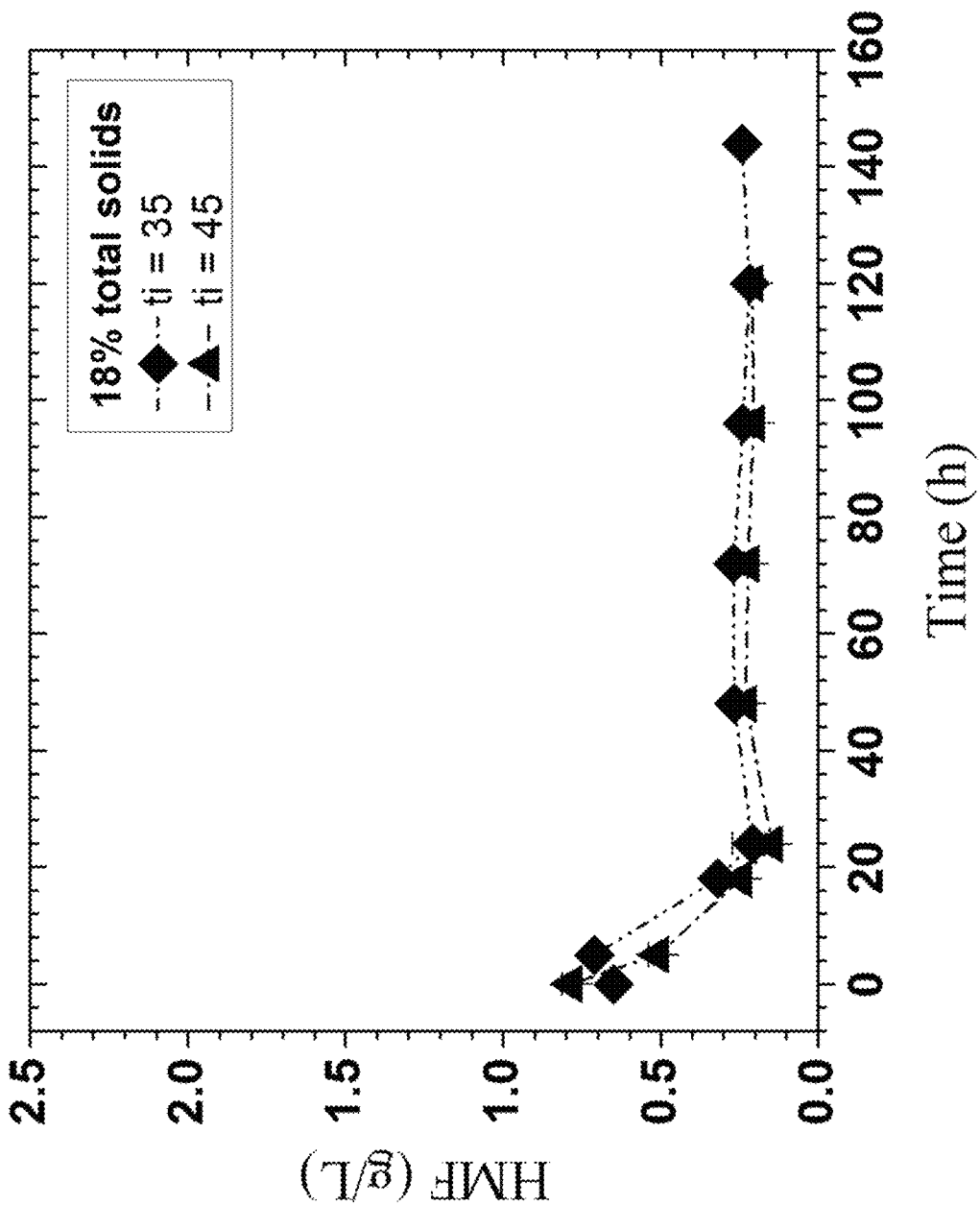
FIG. 14. Time-dependent HMF metabolization in fermentation at total solids loading of 18% using SPORL pretreated whole slurry Douglas-fir forest residue (FS10): Comparisons between two pH profiling SPORL pretreatments with acid injection delay time $t_i$=35 and 45 min respectively.
Figure 15:
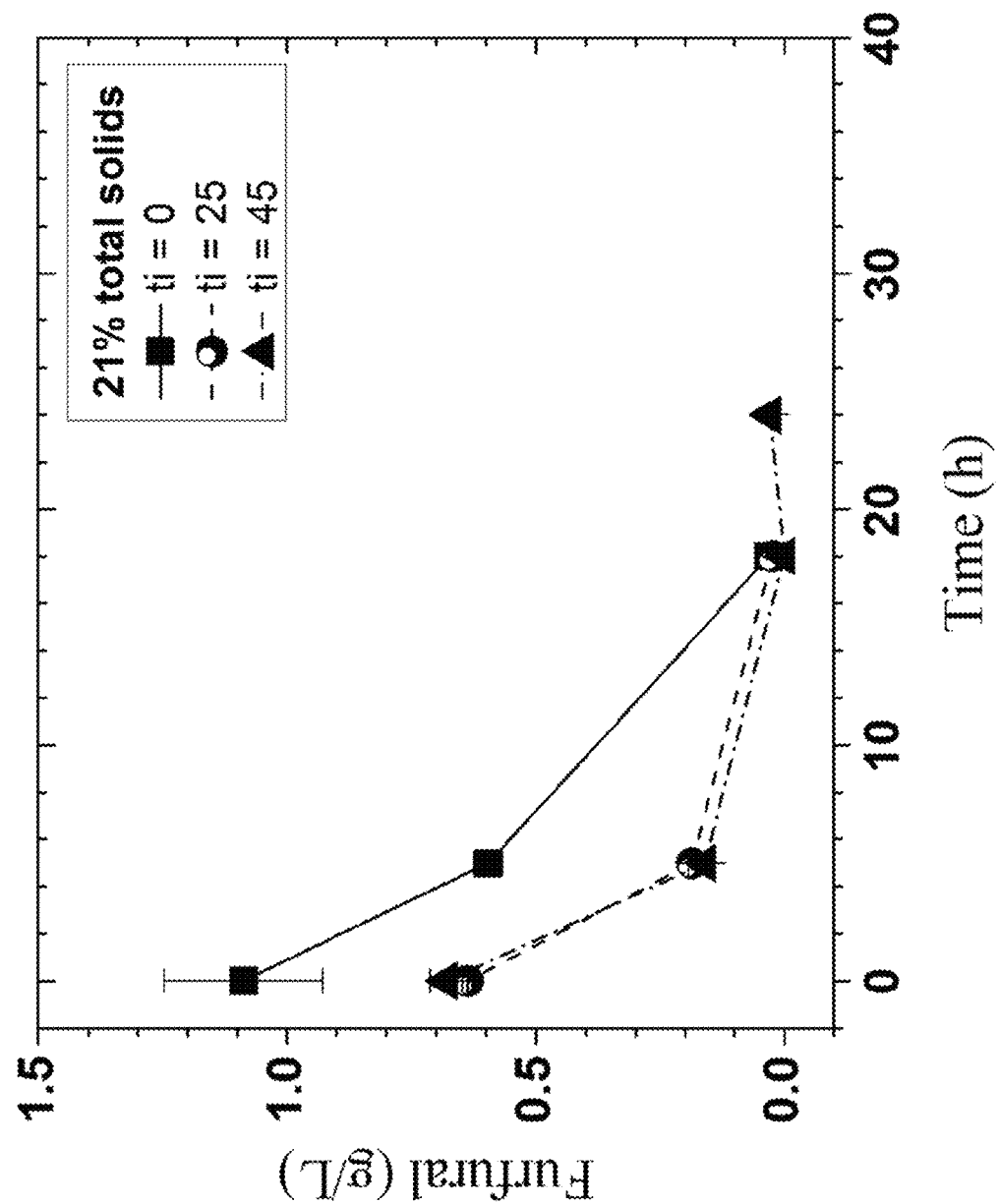
FIG. 15. Time-dependent furfural metabolization in fermentation at total solids loading of 21% using SPORL pretreated whole slurry Douglas-fir forest residue (FS10): Comparisons between pH profiling SPORL pretreatments with acid injection delay time $t_i$=25 and 45 min with the control pretreatment with $t_i$=0.
Figure 16:
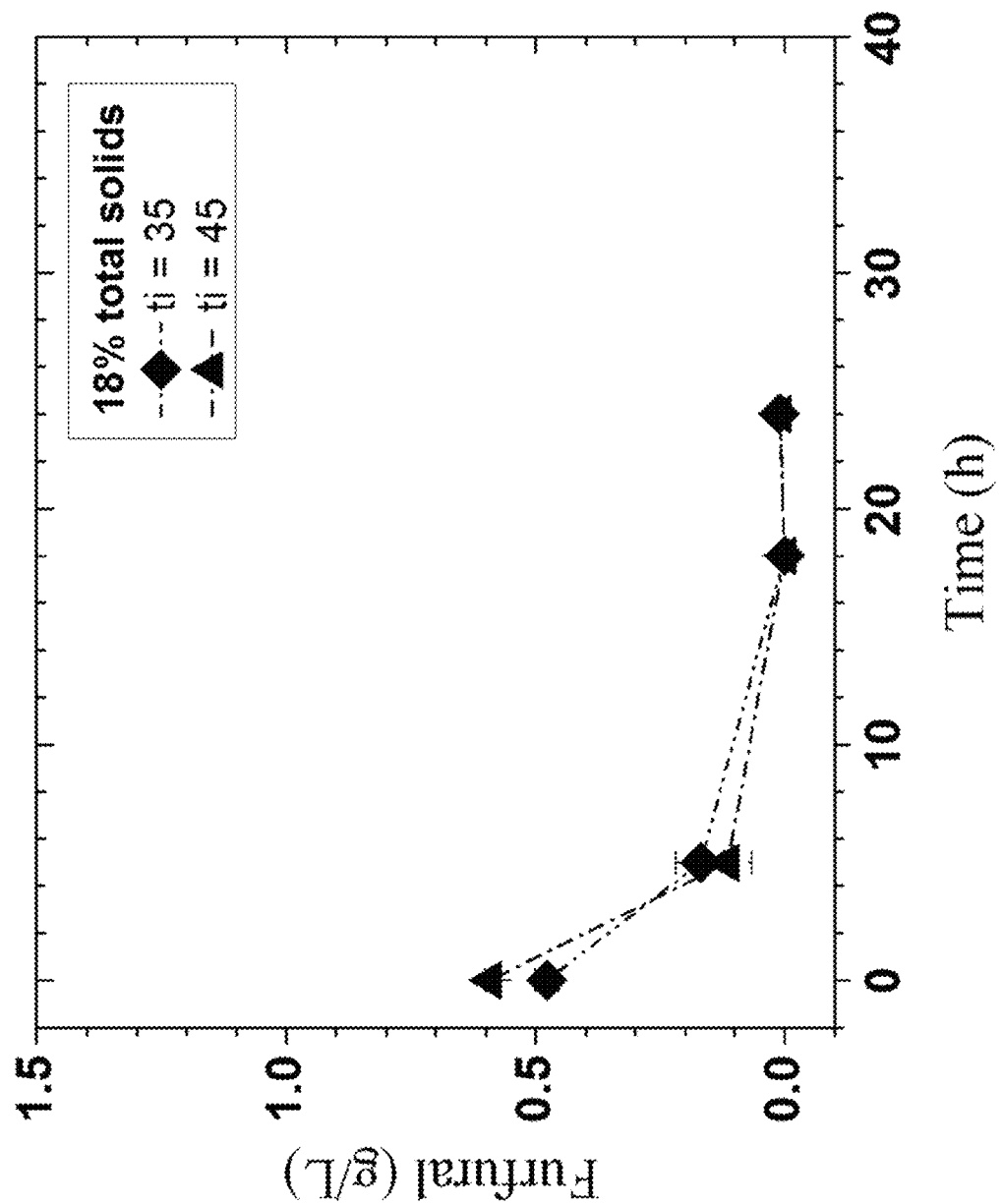
FIG. 16. Time-dependent furfural metabolization in fermentation at total solids loading of 18% using SPORL pretreated whole slurry Douglas-fir forest residue (FS10): Comparisons between two pH profiling SPORL pretreatments with acid injection delay time $t_i$=35 and 45 min respectively.

Simultaneous enzymatic saccharification and combined fermentation (SSCombF) of the pretreated whole slurry (solids plus pretreatment spent liquor) were conducted at 21 and 18% total solids loading. The reduced furans and acetic acid formation in pH profile runs facilitated fermentation which can be seen from the ethanol productivity, although glucose consumptions were not much affected (TABLE IV). The pH profile runs also resulted in a significantly higher final terminal ethanol concentration and yield (TABLE IV, FIGS. 7 and 8). The acid injection time did not significantly affect glucose consumption in fermentation (FIGS. 9 and 10, TABLE IV). Similarly, acid injection time did not significantly affect mannose consumption either (FIGS. 11 and 12). However, the longer delay time of $t_i$=45 min in acid injection slightly reduced ethanol yield compared to the $t_i$=25 min run (TABLE IV). The yield of $t_i$=45 min run still produced more ethanol than the control run. An ethanol yield of 297 L/tonne FS10 forest residue or 73.1% theoretical was achieved from the $t_i$=25 min run vs only 214 L/tonne residue or 52.8% theoretical for the control run. The low furan formation in the pH profile runs also result in lower furan concentration in the fermentation broth in early stages of the fermentation (<40 h), as shown in FIGS. 13-16. This demonstrates that pH profiling reduced furan formation and improved ethanol production.

TABLE IV

Comparisons of fermentation performance among pretreatment with and without active pH control.

|  | Control $t_i$ = 0 | pH profiling $t_i$ = 25 min | pH profiling $t_i$ = 45 min |
|---|---|---|---|
| Average fermentation performance measure (g L$^{-1}$ h$^{-1}$) | | | |
| Glucose consumption (48 h) | −0.59 ± 0.08 | −0.56 ± 0.03 | −0.64 ± 0.03 |
| Ethanol Productivity (48 h) | 0.53 ± 0.03 | 0.55 ± 0.01 | 0.56 ± 0.01 |
| HMF metabolization (24 h) | −0.05 ± 0.002 | −0.03 ± 0.002 | −0.02 ± 0.006 |
| Maximal ethanol production | | | |
| Terminal ethanol concentration (g L$^{-1}$) | 38.6 ± 7.5 | 48.9 ± 1.4 | 45.9 ± 4.6 |
| Ethanol yield (g g sugar$^{-1}$)$^a$ | 0.390 ± 0.076 | 0.494 ± 0.014 | 0.460 ± 0.046 |
| Ethanol yield (L tonne wood$^{-1}$) | 215 ± 42 | 297 ± 9 | 259 ± 26 |
| Ethanol yield (% theoretical)$^b$ | 52.8 ± 10.3 | 73.1 ± 2.1 | 63.7 ± 6.4 |

$^a$based on the total of glucan, mannan, xylan in the pretreated-solids and glucose, mannose, and xylose in the pretreatment spent liquor.
$^b$theoretical yield (406 L tonne wood$^{-1}$) based on total glucan, mannan, xylan in the untreated forest residue of FS10

Example 2

Forest Residue of Douglas-Fir (FS10)—Initial pH of 10.0 pH Profiling Pretreatment—Initial pH=10.0

In this example, the initial pH was increased to an alkaline range. Sodium sulfite was used to achieve an initial pH of approximately 10.0. Sulfuric acid was applied through injection into the digester at two different times $t_i$ during pretreatment. Again, the total chemical loadings, i.e., sodium sulfite (S) and sulfuric acid (A) on oven dry wood base, total pretreatment duration $t_T$, and liquid to wood ratio were the same for all three runs, so that comparisons could be made to demonstrate the advantages of the pH profiling concept. On a molar basis, the sulfite loading applied in this example was the same as that used in Example 1. The pretreatment conditions are listed in TABLE II.

For practical applications, one can also start with hydroxide in the first stage or the beginning of the pretreatment, rather than sodium sulfite. Then $SO_2$ can be injected continuously or at multiple points in the pretreatment, rather than injecting sulfuric acid, to reduce the pH in the acid range. The hydroxide and $SO_2$ will form sulfite to sulfonate and solubilize lignin. The acidic pH condition will also remove hemicelluloses to produce pretreated lignocelluloses with good enzymatic digestibility.

Component Mass Balance of Pretreatments

The key wood component yields from the pretreated washed solids and pretreatment hydrolysates (spent liquors) are again listed in FIG. 19 for the control and pH profiling pretreatments with initial pH=10.0. Similarly, pH profiling runs increased delignification, i.e., lignin yield on washed solids was reduced from 19% for the control run to approximately 15% for the two pH profiling runs. pH profiling significantly reduced hemicellulose removal. Specifically, xylan and mannan yields were increased from 1.3% and 1.5% to approximately 2.5% and 6.3%, respectively, for the pH profiling run with $t_i$=25 min, and 2.9% and 7.1% for the run with $t_i$=45 min. pH profiling also reduced monomeric xylose and mannose yields in the spent liquor. The reduction of furan formation by pH profiling was very significant (FIG. 19). HMF and furfural measured as hexosan and pentosan was reduced from 0.9 and 2.2% respectively, to less than 0.5%. However, the significantly reduced removal of hemicelluloses negatively impacted the enzymatic cellulose saccharification by a significant amount. Therefore, this example demonstrates the significant reduction of furan formation, using an initial pH=10.0 in pH profiling pretreatment can be further optimized by reducing the duration of the first stage of the pretreatment, or by injecting more acid to increase hemicellulose removal to improve substrate enzymatic digestibility.

The negative saccharification results might also be affected by acid loss in experimentation due to improper injection of acid.

Example 3

Forest Residue of Douglas-Fir (FS10)—Pilot Scale Demonstration

Figure 17:
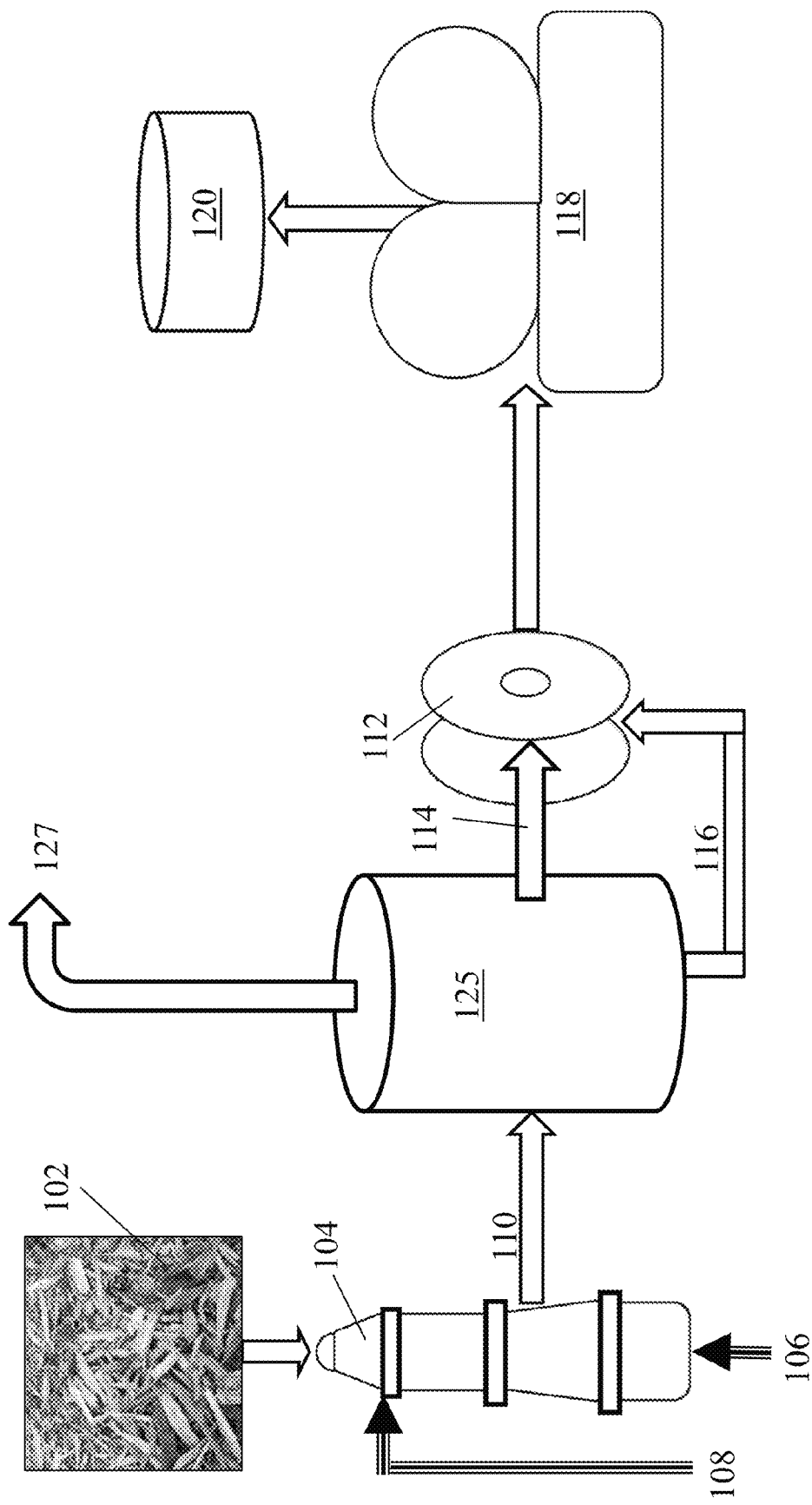
FIG. 17. Schematic flow diagram for the pilot scale evaluation of the present invention.

In this example, pH profiling to reduce furan formation was demonstrated using the pilot scale facility. A charge of 52.6 kg of FS10 was loaded into a 14 ft$^3$ pilot scale rotating digester. The same chemical loading of 12% sodium bisulfate was used initially. The digester was heated by a steam jacket. The heat-up period to 165° C. was approximately 35 min. Sulfuric acid was injected into the digester at 28 min after the heat-up period using pressurized nitrogen. The final acid charge on oven dry wood was 2.2%, the same as the control run conducted at lab scale experiment in Example 1. The pretreatment time was 65 min, shorter than the 75 min used at laboratory scale experiments described in Example 1. This was done to avoid over pretreatment since a longer heat-up period occurred at the pilot scale. At the end of pretreatment, the wood chips was discharged into a blow tank 125 (FIG. 17) by the pressure inside the digester. The blow tank was connected to a scrubber 127 for $SO_2$ removal and recovery for reuse. The pretreated chips were then collected after cooling. Pretreatment spent liquor 116 was also collected from the blow tank. A very small amount of wood chips remained in the digester and was washed out for complete mass balance. A schematic flow diagram of the pilot scale experiment is shown in FIG. 17.

Figure 18:
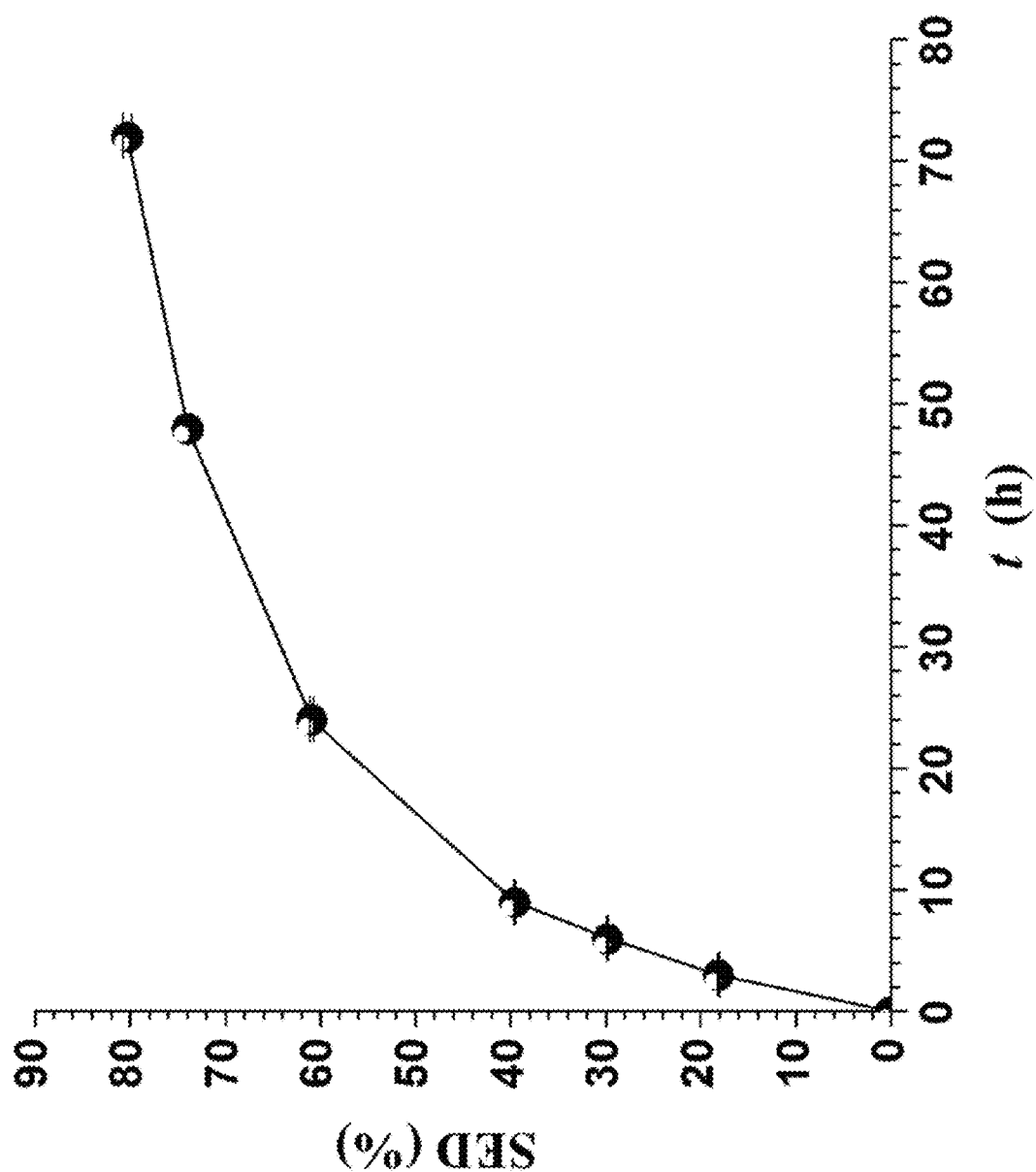
FIG. 18. Time dependent enzymatic saccharification efficiency of pH-profiling SPORL pretreated Douglas-fir forest residue at the pilot scale (FS10).

Enzymatic hydrolysis of washed pretreated substrate was conducted at 10% solids using CTec3 at 15 FPU/g glucan. Excellent saccharification was achieved as represented by SED and shown in FIG. 18. The measured furan concentration in the spent liquor was very low at 0.52 g/L for HMF and 0.55 g/L for furfural. This level of furans will not pose any difficulties for fermentation using conventional strain of yeast as was demonstrated previously with total furan concentration of 4.5 g/L. (See, Zhou H, Zhu J Y, Luo X, Leu S-Y, Wu X, Gleisner R, Dien B S, Hector R E, Yang D, Qiu X and others. 2013b. Bioconversion of beetle-killed lodgepole pine using SPORL: Process scale-up design, lignin coproduct, and high solids fermentation without detoxification. Ind Eng Chem Res 52(45):16057-16065.) A total mass balance analysis was conducted as shown in Table V, which is shown in FIG. 20. Total glucose recovery of 81% was achieved, but HMF and furfural concentration was each only approximately 0.5 g/L in the hemicellulose sugar stream.

The word "illustrative" is used herein to mean serving as an example, instance, or illustration. Any aspect or design described herein as "illustrative" is not necessarily to be construed as preferred or advantageous over other aspects or designs. Further, for the purposes of this disclosure and unless otherwise specified, "a" or "an" means "one or more". Still further, the use of "and" or "or" is intended to include "and/or" unless specifically indicated otherwise.

The foregoing description of illustrative embodiments of the invention has been presented for purposes of illustration and of description. It is not intended to be exhaustive or to limit the invention to the precise form disclosed, and modifications and variations are possible in light of the above teachings or may be acquired from practice of the invention. The embodiments were chosen and described in order to explain the principles of the invention and as practical applications of the invention to enable one skilled in the art to utilize the invention in various embodiments and with various modifications as suited to the particular use contemplated. It is intended that the scope of the invention be defined by the claims appended hereto and their equivalents.

What is claimed is:

1. A method of pretreating lignocellulosic biomass, the method comprising:
    a) mixing the lignocellulosic biomass with either a sulfite solution having an initial pH of at least about 3 or a hydroxide solution having an initial pH of at least about 9, as measured at room temperature, and maintaining the mixture at a temperature in the range from about 150° C. to about 200° C. for a first treatment period; and
    b) subsequently decreasing the pH of the intact mixture of step a) to a pH in the range from about 1 to less than 3 by introducing a pH-reducing agent into the mixture and maintaining the mixture at a temperature in the range from about 150° C. to about 200° C. for a second treatment period to provide a treated product comprising pretreated biomass solids and a process liquor.

2. The method of claim 1, wherein the method removes no greater than about 60% by weight of the lignin present in the lignocellulosic biomass.

3. The method of claim 2, wherein the process liquor comprises no more than about 15 g of carbohydrate degradation products/kg of lignocellulosic biomass.

4. The method of claim 3, wherein the process liquor comprises no more than about 6 g of furan/kg of lignocellulosic biomass.

5. The method of claim 4, wherein the lignocellulosic biomass has a lignin content of at least 15% by weight.

6. The method of claim 1, wherein the process liquor comprises no more than about 15 g of carbohydrate degradation products/kg of lignocellulosic biomass.

7. The method of claim 6, wherein the process liquor comprises no more than about 6 g of furan/kg of lignocellulosic biomass.

8. The method of claim 1, wherein the lignocellulosic biomass is mixed with the sulfite solution; the sulfite solution has a pH in the range from about 3 to about 5, as measured at room temperature; and the pH-reducing agent is sulfur dioxide, an acid or a combination of both.

9. The method of claim 1, wherein the lignocellulosic biomass is mixed with the sulfite solution; the sulfite solution has a pH in the range from about 9 to about 11, as measured at room temperature; and the pH-reducing agent is sulfur dioxide, an acid or a combination of both.

10. The method of claim 1, wherein the lignocellulosic biomass is mixed with the hydroxide solution and the pH reducing agent is sulfur dioxide.

11. The method of claim 10, wherein the step of decreasing the pH of the mixture to a pH in the range from about 1 to less than 3 comprises at least two sequential injections of the sulfur dioxide into the mixture, wherein the mixture has a pH in the range from about 3 to about 7 after the first of the at least two injections and a pH in the range from about 1 to about 2 after the last of the at least two injections.

12. The method of claim 11, wherein the mixture has a pH in the range from about 3 to about 5 after the first of the at least two injections.

13. The method of claim 10, wherein the step of decreasing the pH of the mixture to a pH in the range from about 1 to less than 3 comprises continuously injecting the pH reducing agent into the mixture to provide a continuous pH adjustment until the mixture has a pH in the range from about 1 to about 2.

14. The method of claim 1, wherein the pH-reducing agent is sulfur dioxide, an acid, or the combination of both.

15. The method of claim 1, wherein the lignocellulosic biomass has a lignin content of at least 10% by weight.

16. The method of claim 1, wherein the step of decreasing the pH of the mixture to a pH in the range from about 1 to less than 3 by introducing a pH-reducing agent into the mixture comprises introducing two or more sequential injections of the pH-reducing agent into the mixture.

17. A method of producing ethanol from lignocellulosic biomass, the method comprising:
    a) mixing the lignocellulosic biomass with either a sulfite solution having an initial pH of at least about 3 or a hydroxide solution having an initial pH of at least about 9, as measured at room temperature, and maintaining the mixture at a temperature in the range from about 150° C. to about 200° C. for a first treatment period;
    b) subsequently decreasing the pH of the intact mixture of step a) to a pH in the range from about 1 to less than 3 by introducing a pH-reducing agent into the mixture and maintaining the mixture at a temperature in the range from about 150° C. to about 200° C. for a second treatment period to provide a treated product comprising pretreated biomass solids and a process liquor; and
    subjecting the pretreated product to enzymatic saccharification and fermentation to produce ethanol.

18. The method of claim 17, wherein the method removes no greater than about 60% by weight of the lignin present in the lignocellulosic biomass.

19. The method of claim 18, wherein the process liquor comprises no more than about 15 g of carbohydrate degradation products/kg of lignocellulosic biomass.

20. The method of claim 19, wherein the process liquor comprises no more than about 6 g of furan/kg of lignocellulosic biomass.

21. The method of claim 17, wherein the lignocellulosic biomass is mixed with the sulfite solution; the sulfite solution has a pH in the range from about 3 to about 5, as measured at room temperature; and the pH-reducing agent is sulfur dioxide, an acid or a combination of both.

22. The method of claim 17, wherein the lignocellulosic biomass is mixed with the sulfite solution; the sulfite solution has a pH in the range from about 9 to about 11, as measured at room temperature; and the pH-reducing agent is sulfur dioxide, an acid or a combination of both.

23. The method of claim 17, wherein the lignocellulosic biomass is mixed with the hydroxide solution and the pH reducing agent is sulfur dioxide.

24. The method of claim 17, wherein the step of decreasing the pH of the mixture to a pH in the range from about 1 to less than 3 comprises at least two sequential injections of the sulfur dioxide into the mixture, wherein the mixture has a pH in the range from about 3 to about 7 after the first of the at least two injections and a pH in the range from about 1 to about 2 after the last of the at least two injections.

25. The method of claim 24, wherein the mixture has a pH in the range from about 3 to about 5 after the first of the at least two injections.

26. The method of claim 17, wherein the step of decreasing the pH of the mixture to a pH in the range from about 1 to less than 3 comprises continuously injecting the pH reducing agent into the mixture to provide a continuous pH adjustment until the mixture has a pH in the range from about 1 to about 2.

* * * * *